US009339656B2

(12) United States Patent
Ghosh

(10) Patent No.: US 9,339,656 B2
(45) Date of Patent: May 17, 2016

(54) METHODS AND SYSTEMS FOR IDENTIFYING REASONS FOR INEFFECTIVE LEFT VENTRICULAR CAPTURE IN CARDIAC RESYNCHRONIZATION THERAPY BASED ON EGM MORPHOLOGY

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/193,186

(22) Filed: Feb. 28, 2014

(65) Prior Publication Data
US 2015/0246235 A1 Sep. 3, 2015

(51) Int. Cl.
| A61N 1/37 | (2006.01) |
| A61N 1/05 | (2006.01) |
| A61N 1/36 | (2006.01) |
| A61B 5/00 | (2006.01) |
| A61B 5/0452 | (2006.01) |
| A61N 1/372 | (2006.01) |

(52) U.S. Cl.
CPC .......... *A61N 1/3712* (2013.01); *A61B 5/04525* (2013.01); *A61B 5/4836* (2013.01); *A61B 5/6869* (2013.01); *A61B 5/7282* (2013.01); *A61N 1/37247* (2013.01)

(58) Field of Classification Search
None
See application file for complete search history.

(56) References Cited

U.S. PATENT DOCUMENTS

| 4,428,378 A | 1/1984 | Anderson et al. |
| 4,955,376 A | 9/1990 | Callaghan et al. |
| 5,052,388 A | 10/1991 | Sivula et al. |
| 5,324,310 A | 6/1994 | Greeninger et al. |
| 5,411,524 A | 5/1995 | Rahul |
| 5,766,230 A | 6/1998 | Routh et al. |
| 5,954,756 A | 9/1999 | Hemming et al. |
| 6,473,649 B1 * | 10/2002 | Gryzwa et al. ................. 607/28 |
| 6,643,549 B1 | 11/2003 | Bradley et al. |
| 6,704,598 B2 | 3/2004 | Ding et al. |
| 7,123,963 B2 | 10/2006 | Sawchuk et al. |
| 7,139,610 B2 | 11/2006 | Ferek-Petric |

(Continued)

OTHER PUBLICATIONS (PCT/US2013/072974) PCT Notification of Transmittal of the International Search Report and the Written Opinion of the International Searching Authority.

(Continued)

*Primary Examiner* — Brian T Gedeon
*Assistant Examiner* — Ankit Tejani
(74) *Attorney, Agent, or Firm* — Carol F. Barry

(57) ABSTRACT

The present disclosure pertains to cardiac pacing methods and systems, and, more particularly, to cardiac resynchronization therapy (CRT). In particular, the present disclosure pertains to determining the efficacy of CRT through use of an effective capture test (ECT). One or more embodiments comprises sensing a signal in response to a ventricular pacing stimulus. Through signal processing, a number of features are parsed from the signal. Exemplary features parsed from the signal include a maximum amplitude, a maximum time associated with the maximum amplitude, a minimum amplitude, and a minimum time associated with the minimum amplitude. The data is evaluated through use of the ECT. By employing the ECT, efficacy of CRT is easily and automatically evaluated. In one or more other embodiments, the reason for ineffective capture is displayed to the user. Exemplary reasons for ineffective capture include pseudo-fusion pacing and lack of capture of the ventricle.

20 Claims, 18 Drawing Sheets

(56) References Cited

U.S. PATENT DOCUMENTS

| | | |
|---|---|---|
| 7,424,323 B1 | 9/2008 | Reiss et al. |
| 7,515,959 B2 | 4/2009 | Hess |
| 7,684,863 B2 | 3/2010 | Parikh et al. |
| 7,715,917 B2 | 5/2010 | Chinchoy et al. |
| 7,831,303 B2 | 11/2010 | Rueter et al. |
| 7,848,807 B2 | 12/2010 | Wang |
| 7,908,004 B1 | 3/2011 | Gill et al. |
| 7,953,482 B2 | 5/2011 | Hess |
| 7,970,473 B2 | 6/2011 | Nabutovsky et al. |
| 8,046,065 B2 | 10/2011 | Burnes et al. |
| 8,271,087 B2 | 9/2012 | Sathaye et al. |
| 8,489,188 B2 | 7/2013 | Giorgis et al. |
| 8,738,132 B1 * | 5/2014 | Ghosh et al. .............. 607/28 |
| 8,750,998 B1 * | 6/2014 | Ghosh et al. .............. 607/28 |
| 8,750,999 B1 * | 6/2014 | Ghosh et al. .............. 607/28 |
| 2004/0116974 A1 | 6/2004 | Obel |
| 2006/0155338 A1 | 7/2006 | Mongeon et al. |
| 2009/0276001 A1 | 11/2009 | Busacker et al. |
| 2010/0016914 A1 | 1/2010 | Mullen et al. |
| 2010/0057156 A1 | 3/2010 | Chow |
| 2010/0121397 A1 | 5/2010 | Cholette |
| 2010/0137935 A1 | 6/2010 | Parikh et al. |
| 2011/0172728 A1 | 7/2011 | Wang |
| 2012/0191154 A1 | 7/2012 | Ryu et al. |
| 2013/0090702 A1 | 4/2013 | Mongeon et al. |
| 2014/0114372 A1 * | 4/2014 | Ghosh et al. .............. 607/28 |
| 2014/0163633 A1 * | 6/2014 | Ghosh et al. .............. 607/28 |

OTHER PUBLICATIONS

"Left Ventricular Capture Management", Medtronic, Inc. article, Mar. 2006.

* cited by examiner

METHODS AND SYSTEMS FOR IDENTIFYING REASONS FOR INEFFECTIVE LEFT VENTRICULAR CAPTURE IN CARDIAC RESYNCHRONIZATION THERAPY BASED ON EGM MORPHOLOGY

CROSS-REFERENCE TO RELATED APPLICATION

Cross-reference is hereby made to the commonly-assigned related U.S. applications, Co-pending U.S. patent application Ser. No. 13/707,366 entitled "EFFECTIVE CAPTURE" filed by Subham Ghosh et al. and assigned to the same assignee of the present disclosure; Co-pending U.S. patent application Ser. No. 13/707,391 entitled "EFFECTIVE CAPTURE" filed by Subham Ghosh et al. and assigned to the same assignee of the present disclosure; Co-pending U.S. patent application Ser. No. 13/707,404 entitled "EFFECTIVE CAPTURE" filed by Subham Ghosh et al. and assigned to the same assignee of the present disclosure; Co-pending U.S. patent application Ser. No. 13/707,458 entitled "EFFECTIVE CAPTURE" filed by Subham Ghosh et al. and assigned to the same assignee of the present disclosure.

FIELD

The present disclosure pertains to cardiac pacing methods and systems, and, more particularly, to cardiac resynchronization therapy (CRT).

BACKGROUND

Cardiac resynchronization cardiac pacing devices operate by either delivering pacing stimulus to both ventricles or to one ventricle with the desired result of a more or less simultaneous mechanical contraction and ejection of blood from the ventricles. Ideally, each pacing pulse stimulus delivered to a ventricle evokes a response from the ventricle. Delivering electrical stimuli that causes the ventricle to respond is commonly referred to as capturing a ventricle. For a variety of reasons, cardiac pacing systems may not achieve effective capture of a ventricle. For example, a pacing lead and/or electrode may not be placed in an optimal location. Sensed atrioventricular delay (SAV), paced atrioventricular delay (PAV), right ventricular pre-excitation may also affect whether a ventricle is effectively captured. Additionally, after the medical device has been implanted, migration or dislodgement of the pacing lead may occur. It is desirable to develop additional systems and methods that automatically determine optimal effective capture of a ventricle.

DETAILED DESCRIPTION OF EXEMPLARY EMBODIMENTS

Figure 1:
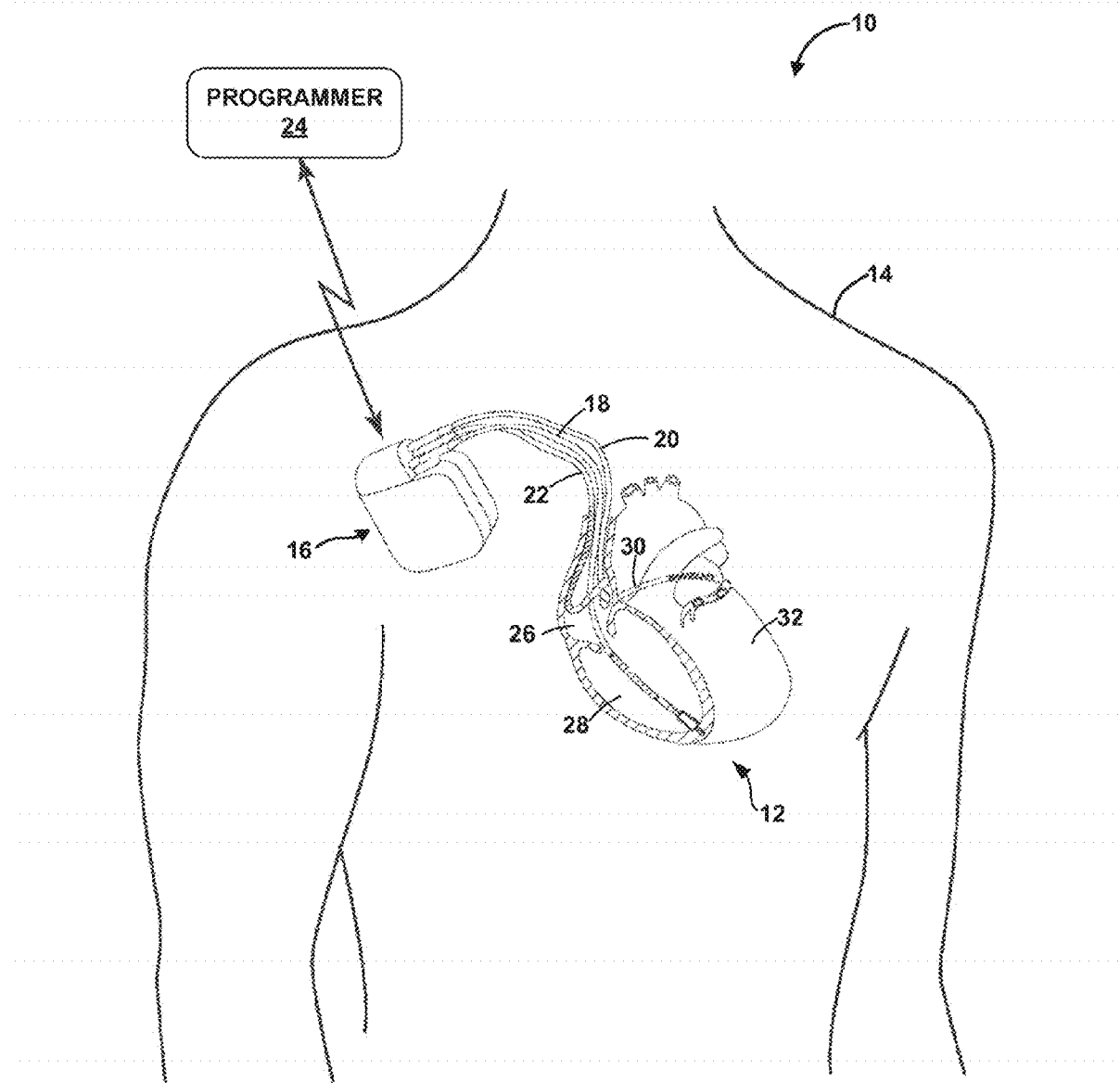
FIG. 1 is a diagram of an exemplary system including an exemplary implantable medical device (IMD).

In the following detailed description, references are made to illustrative embodiments for carrying out methods of confirming pacing capture of ventricular pacing stimulation. It is understood that other embodiments may be utilized without departing from the scope of the invention. For example, the invention is disclosed in detail herein in the context of a bi-ventricular cardiac resynchronization therapy (CRT) delivery.

Exemplary methods, devices, and systems shall be described with reference to FIGS. 1-17. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale.

The term "effective capture test," employs elements parsed from a signal sensed from the ventricle. A sensed signal from a ventricle includes a maximum amplitude (Max), a maximum time (Tmax) associated with the maximum amplitude (Max), a minimum amplitude (Min), and a minimum time (Tmin) associated with the minimum amplitude. The effective capture test is based upon one or more of:

$$Tmax - Tmin > 30 \text{ ms} \qquad (1)$$

$$0.2 < |Max - a\ baseline\ (BL)|/|BL - Min| < 5; \qquad (2)$$

$$(\text{Max}-\text{BL}|/|\text{Min}-\text{BL}|\leq \text{LL and BL}<|\text{Min}/8|) \quad (3)$$

$$T\text{min}<60 \text{ ms; and} \quad (4)$$

$$\text{Max}-\text{Min}>3.5 \text{ mV.} \quad (5)$$

The effective capture test, typically performed daily, determines whether effective capture of a ventricle is occurring after the implantable medical device has been implanted in a patient. The effective capture test uses ideal pace timing conditions for a few beats during the effective capture test. Ideal pace timing conditions means that the normal pace timing is modified to increase the chances of effective capture. If effective capture is not achieved during ideal pace timing conditions, then effective capture cannot be achieved during normal daily monitoring to pace therapy. Normal daily monitoring to pace therapy is referred to herein as capture monitoring and is typically performed at a rate of 100 beats/hour.

The present disclosure is able to achieve effective capture by delivering pacing stimuli at sufficient energy and at the proper timing, which provides beneficial results over known capture management algorithms. While capture management algorithms are able to artificially modify the timing (i.e., overdrive pace or use very short SAV/PAV), the main focus of capture management algorithms is on sufficient energy delivery of a pacing stimulus. Capture management algorithms generally do not address proper timing and cannot be used to assess effective capture during normal device operation.

In one or more embodiments, the present disclosure determines the efficacy of CRT by sensing a signal in response to a ventricular pacing stimulus. A processor determines whether a positive deflection of the signal precedes a negative deflection of the signal. A determination is made as to whether the ventricular pacing stimulus is capturing the paced ventricle in response to determining whether the positive deflection precedes the negative deflection.

In one or more embodiments, the present disclosure determines the efficacy of CRT by sensing a signal in response to a ventricular pacing stimulus. Through signal processing, a number of features are parsed from the signal such as maximum amplitude, a maximum time associated with the maximum amplitude, a minimum amplitude, and a minimum time associated with the minimum amplitude. Thereafter, a determination is made as to whether the maximum time minus the minimum time is greater than a preselected threshold. In one or more other embodiments, a fraction is calculated. The numerator of the fraction is equal to the maximum amplitude minus a baseline. The denominator is equal to the baseline minus the minimum amplitude. A determination is then made as to whether the fraction is greater than a lower limit and whether the fraction is less than an upper limit. In response to determining whether the fraction is greater than the lower limit and whether the fraction is less than the upper limit, a determination is made as to whether the ventricular pacing stimulus is capturing the paced ventricle. In yet one or more embodiments, a determination is made as whether the minimum time is less than a predetermined time. By employing these simple criteria, efficacy of CRT is easily and automatically evaluated.

In one or more other embodiments, reasons for ineffective capture are displayed to a user on a graphical user interface of a programmer. Exemplary reasons for ineffective capture include fusion-pacing or lack of capture of the ventricle.

FIG. 1 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22 and a programmer 24. The IMD 16 may be, e.g., an implantable pacemaker, cardioverter, and/or defibrillator, that provides electrical signals to the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., pulse wide, amplitude, voltage, burst length, etc. Further, the IMD 16 may be operable to use various electrode configurations to deliver pacing therapy, which may be unipolar or bipolar. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

In some examples, a programmer 24, which may be a handheld computing device or a computer workstation, may be used by a user, such as a physician, technician, another clinician, and/or patient, to communicate with the IMD 16 (e.g., to program the IMD 16). For example, the user may interact with the programmer 24 to retrieve information concerning one or more detected or indicated faults associated within the IMD 16 and/or the pacing therapy delivered therewith. The IMD 16 and the programmer 24 may communicate via wireless communication using any techniques known in the art. Examples of communication techniques may include, e.g., low frequency or radiofrequency (RF) telemetry, but other techniques are also contemplated.

Figure 2:
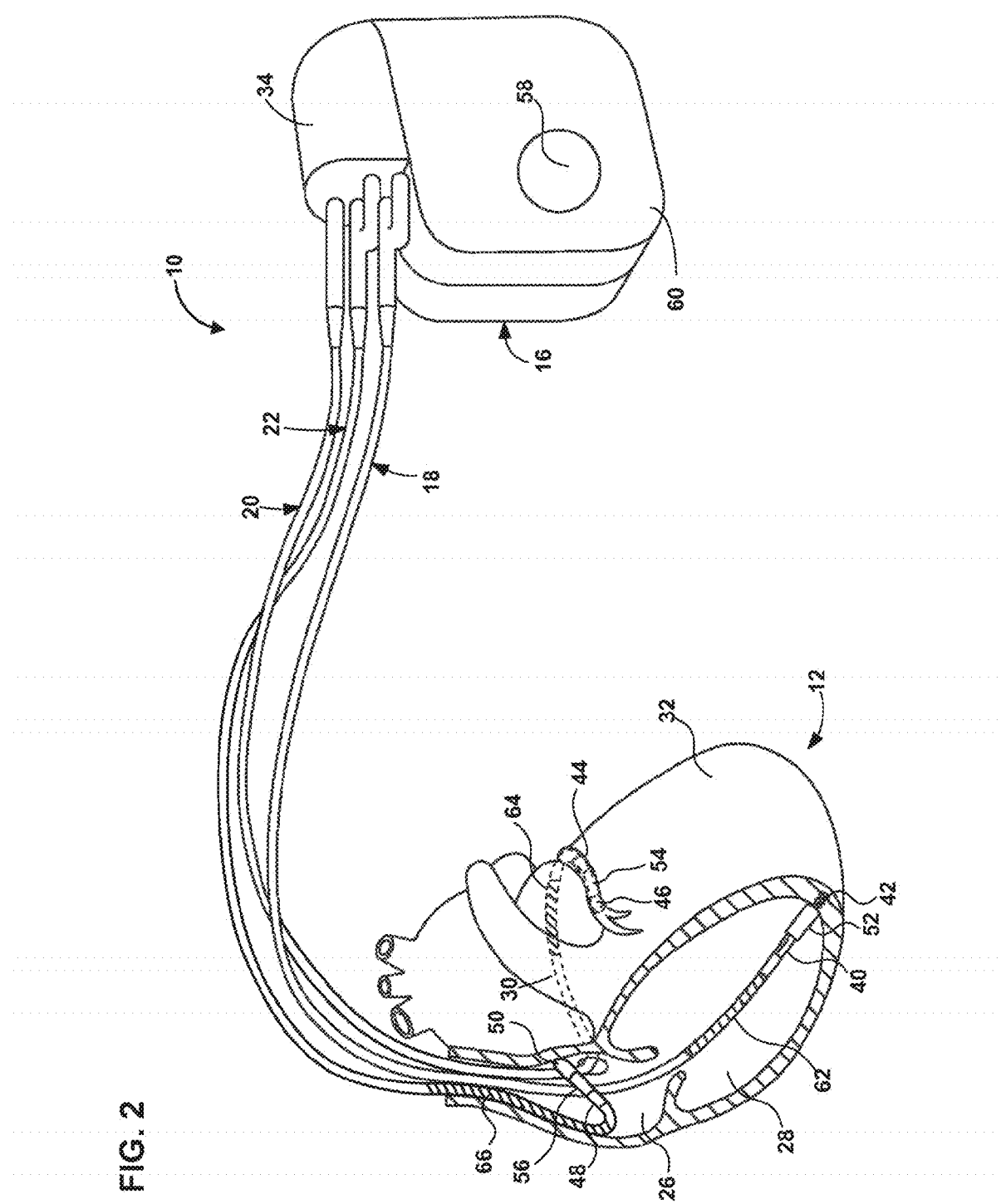
FIG. 2 is a diagram of the exemplary IMD of FIG. 1.

FIG. 2 is a conceptual diagram illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., one or more electrodes to sense or monitor electrical activity of the heart 12 for use in determining effectiveness of pacing therapy), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, the bipolar electrodes 44, 46 are located proximate to a distal end of the lead 20 and the bipolar electrodes 48, 50 are located proximate to a distal end of the lead 22.

The electrodes 40, 44, 48 may take the form of ring electrodes, and the electrodes 42, 46, 50 may take the form of extendable helix tip electrodes mounted retractably within the insulative electrode heads 52, 54, 56, respectively. Each of the electrodes 40, 42, 44, 46, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22.

The electrodes 40, 42, 44, 46, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 46, 48, 50 to cause depolarization of cardiac tissue of the patient's heart 12. In some examples, as illustrated in FIG. 2, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 46, 48, 50 may be used for unipolar sensing or pacing in combination with housing electrode 58. In other words, any of electrodes 40, 42, 44, 46, 48, 50, 58 may be used in combination to form a sensing vector, e.g., a sensing vector that may be used to evaluate and/or analysis the effectiveness of pacing therapy. An example of a configuration sensing and pacing may be seen with respect to U.S. Pat. Application No. 61/580,058 filed Dec. 23, 2011, and assigned to the assignee of the present invention, the disclosure of which is incorporated by reference in its entirety herein as modified by preferably using a LVtip (i.e. electrode 46)-Rvcoil (i.e. electrode 62) for the pacing vector and the sensing vector. It is generally understood by those skilled in the art that other electrodes can also be selected as pacing and sensing vectors. Electrode 44 and 64 refer to the third and fourth LV electrodes in the claims.

As described in further detail with reference to FIGS. 3A-3B, the housing 60 may enclose a therapy delivery module that may include a stimulation generator for generating cardiac pacing pulses and defibrillation or cardioversion shocks, as well as a sensing module for monitoring the patient's heart rhythm. The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity during pacing therapy (e.g., for use in analyzing pacing therapy effectiveness) and may be used in combination with any of electrodes 40, 42, 44, 46, 48, 50, 58. In at least one embodiment, the RV elongated electrode 62 may be used to sense electrical activity of a patient's heart during the delivery of pacing therapy (e.g., in combination with the housing electrode 58 forming a RV elongated, coil, or defibrillation electrode-to-housing electrode vector).

The configuration of the exemplary therapy system 10 illustrated in FIGS. 1-2 is merely one example. In other examples, the therapy system may include epicardial leads and/or patch electrodes instead of or in addition to the transvenous leads 18, 20, 22 illustrated in FIG. 1. Further, in one or more embodiments, the IMD 16 need not be implanted within the patient 14. For example, the IMD 16 may deliver defibrillation shocks and other therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 1-2. Still further, other therapy systems may include a single lead that extends from the IMD 16 into the right atrium 26 or the right ventricle 28, or two leads that extend into a respective one of the right atrium 26 and the right ventricle 28.

Figure 3A:
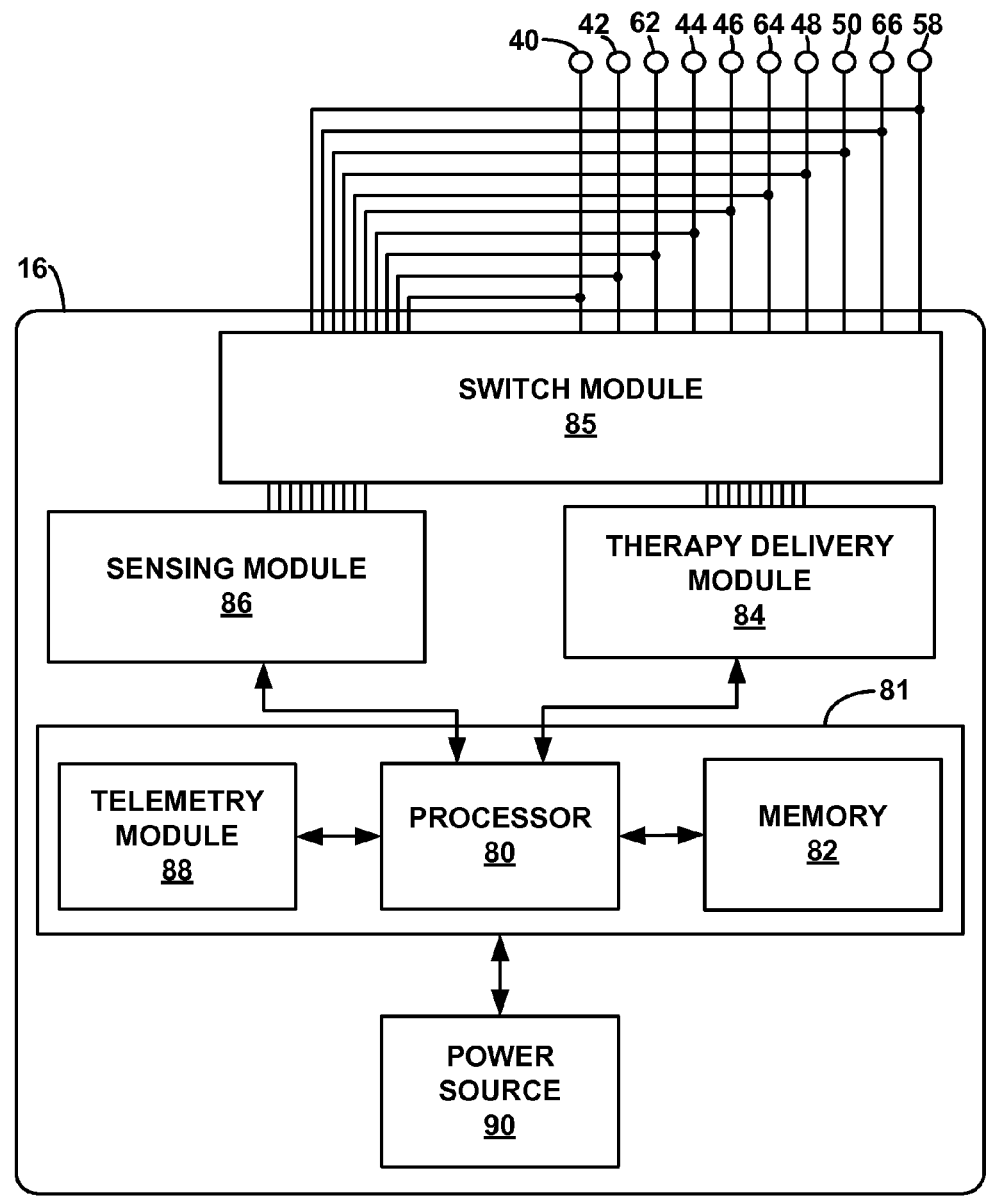
FIG. 3A is a block diagram of an exemplary IMD, e.g., the IMD of FIGS. 1-2.

FIG. 3A is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media. Memory 82 includes computer instructions related to capture management. An exemplary capture management module such as left ventricular capture management (LVCM) is briefly described in U.S. Pat. No. 7,684,863, which is incorporated by reference. As to the delivery of pacing stimuli, capture management algorithms typically focus on sufficient energy delivery of a pacing stimulus.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control the therapy delivery module 84 to deliver electrical stimulus such as, e.g., pacing pulses with the amplitudes, pulse widths, frequency, or electrode polarities specified by the selected one or more therapy programs (e.g., pacing therapy programs, pacing recovery programs, capture management programs, etc.). As shown, the therapy delivery module 84 is electrically coupled to electrodes 40, 42, 44, 46, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 46, 48, 50, 58, 62, 64, 66.

For example, therapy delivery module 84 may deliver pacing stimulus (e.g., pacing pulses) via ring electrodes 40, 44, 48 coupled to leads 18, 20, and 22, respectively, and/or helical tip electrodes 42, 46, and 50 of leads 18, 20, and 22, respectively. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 46, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 46, 48, 50, 58, 62, 64, 66 to monitor electrical activity of the heart 12, e.g., electrocardiogram (ECG)/electrogram (EGM) signals, etc. The ECG/EGM signals may be used to analyze of a plurality of paced events. More specifically, one or more morphological features of each paced event within the ECG/EGM signals may be used to determine whether each paced event has a predetermined level of effectiveness. The ECG/EGM signals may be further used to monitor heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used to, e.g., sense electrical activity of the patient's heart (e.g., one or more electrical vectors of the patient's heart using any combination of the electrodes 40, 42, 44, 46, 48, 50, 58, 62, 64, 66). In some examples, the control module 81 may select the electrodes that function as sensing electrodes via the switch module within the sensing module 86, e.g., by providing signals via a data/address bus. In some examples, the sensing module 86 may include one or more sensing channels, each of which may include an amplifier.

In some examples, sensing module 86 includes a channel that includes an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an EGM. In some examples, the storage of such EGMs in memory 82 may be under the control of a direct memory access circuit. The control module 81 (e.g., using the processor 80) may employ digital signal analysis techniques to characterize the digitized signals stored in memory 82 to analyze and/or classify one or more morphological waveforms of the EGM signals to determine pacing therapy effectiveness. For example, the processor 80 may be configured to determine, or obtain, one more features of one or more sensed morphological waveforms within one of more electrical vectors of the patient's heart and store the one or more features within the memory 82 for use in determining effectiveness of pacing therapy at a later time.

If IMD 16 is configured to generate and deliver pacing pulses to the heart 12, the control module 81 may include a pacer timing and control module, which may be embodied as hardware, firmware, software, or any combination thereof. The pacer timing and control module may include one or more dedicated hardware circuits, such as an ASIC, separate from the processor 80, such as a microprocessor, and/or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within control module 81 may include atrial and ventricular pacing escape intervals, refractory periods during which sensed P-waves and R-waves are ineffective to restart timing of the escape intervals, and/or the pulse widths of the pacing pulses. As another example, the pacer timing and control module may define a blanking period, and provide signals from sensing module 86 to blank one or more channels, e.g., amplifiers, for a period during and after delivery of electrical stimulation to the heart 12. The durations of these intervals may be determined in response to stored data in memory 82.

The pacer timing and control module of the control module 81 may also determine the amplitude of the cardiac pacing pulses.

During pacing, escape interval counters within the pacer timing/control module may be reset upon sensing of R-waves and P-waves. Therapy delivery module 84 (e.g., including a stimulation generator) may include one or more pacing output circuits that are coupled, e.g., selectively by the switch module 85, to any combination of electrodes 40, 42, 44, 46, 48, 50, 58, 62, or 66 appropriate for delivery of a bipolar or unipolar pacing pulse to one of the chambers of heart 12. The control module 81 may reset the escape interval counters upon the generation of pacing pulses by therapy delivery module 84, and thereby control the basic timing of cardiac pacing functions, including anti-tachyarrhythmia pacing.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as the programmer 24 as described herein with respect to FIG. 1. For example, under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer. In at least one embodiment, the telemetry module 88 may be configured to transmit an alarm, or alert, if the pacing therapy becomes ineffective or less effective (e.g., does not have a predetermined level of effectiveness).

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

A pacing (e.g., for LV and/or BV pacing) ratio or percentage, which is the number of paced heart beats divided by the total number of heart beats, often expressed as a percentage of the total number of heart beats, may be a useful metric for evaluating the effectiveness of CRT but, in many cases, it may be misleading because a high pacing ratio or percentage may not necessarily mean that CRT is effective if, e.g., ventricular pacing fails to properly alter electrical activation patterns. Automatic beat-to-beat analysis of the evoked response (e.g., paced QRS complexes) in monitored EGM signals may be used to determine whether the paced heartbeat was effectively paced, and hence, to provide more resolution to a pacing ratio. For example, the heartbeats that were paced but determined to not be effectively paced (e.g., depending on the degree of fusion between intrinsic and paced activation, etc.) may be excluded from the pacing ratio thereby providing a more accurate metric of pacing efficacy and/or efficiency, which may referred to as a pacing effectiveness ratio.

A feature-based classification may enable beat-to-beat rhythm classification in a device (e.g., IMD 16) employing cardiac pacing (e.g., left ventricular fusion pacing, biventricular pacing, etc.) and may add value to the device by providing useful diagnostic indices to a physician. The computational price involved in such feature-based beat-to-beat classifications may be minimal and may be implemented within the architecture of devices such as the IMD 16 described herein with reference to FIGS. 1-3B. For example, the exemplary methods described herein may combine algebraic operations and comparisons and/or may require a single normalization per beat compared to multiple intensive mathematical operations and normalizations that are often required for detailed template matching algorithms.

Figure 3B:
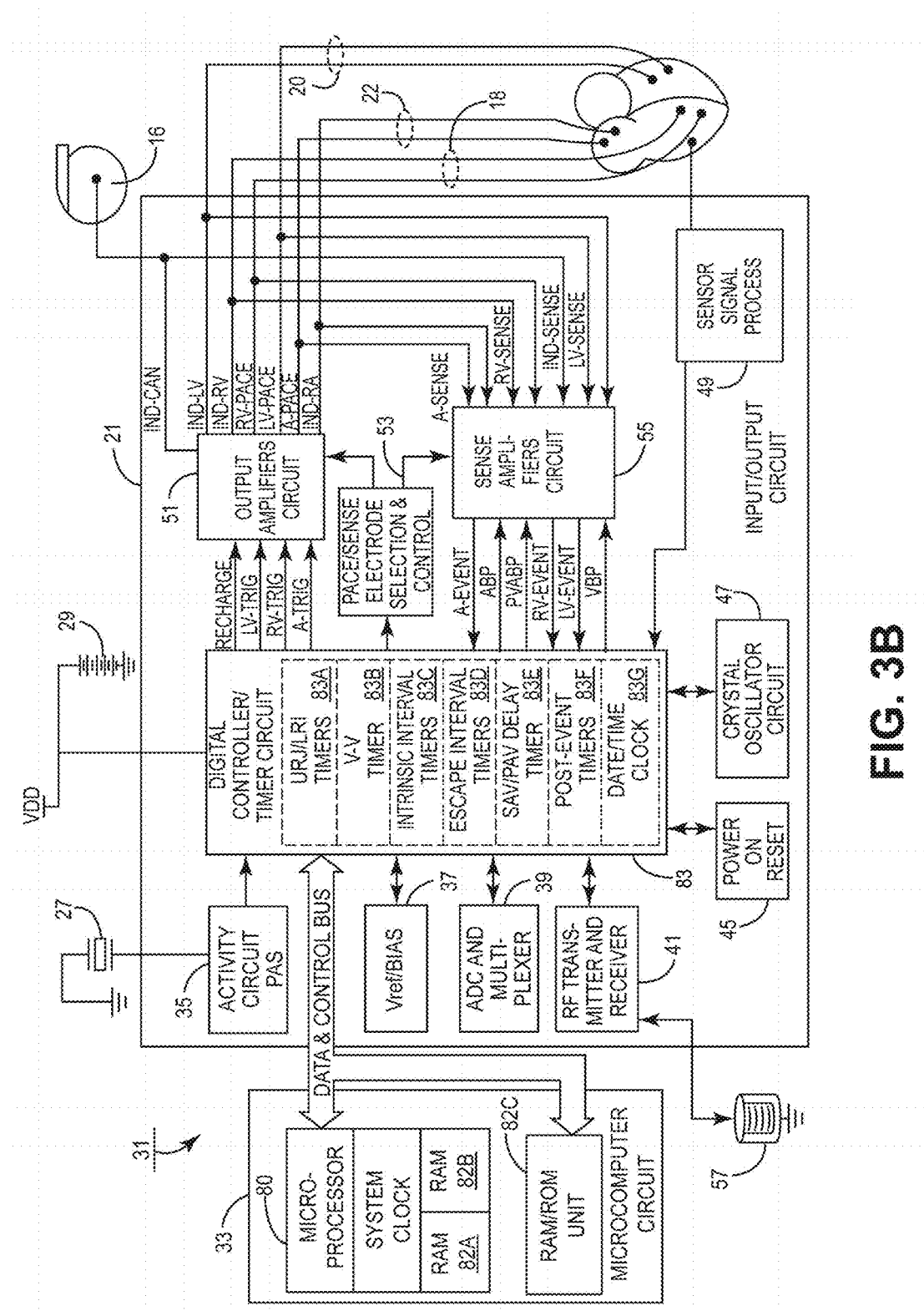
FIG. 3B is yet another block diagram of one embodiment of IMD (e.g. IPG) circuitry and associated leads employed in the system of FIG. 2 for providing three sensing channels and corresponding pacing channels that selectively functions in a ventricular pacing mode providing ventricular capture verification.

FIG. 3B is yet another embodiment of a functional block diagram for IMD 16. FIG. 3B depicts bipolar RA lead 22, bipolar RV lead 18, and bipolar LV CS lead 20 without the LA CS pace/sense electrodes 28 and 30 coupled with an IPG circuit 31 having programmable modes and parameters of a bi-ventricular DDD/R type known in the pacing art. In turn, the sensor signal processing circuit 49 indirectly couples to the timing circuit 83 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 83, the output amplifiers circuit 51, the sense amplifiers circuit 55, the RF telemetry transceiver 41, the activity sensor circuit 35 as well as a number of other circuits and components described below.

Crystal oscillator circuit 47 provides the basic timing clock for the pacing circuit 21, while battery 29 provides power. Power-on-reset circuit 45 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21, while analog to digital converter ADC and multiplexer circuit 39 digitizes analog signals and voltage to provide real time telemetry if a cardiac signals from sense amplifiers 55, for uplink transmission via RF transmitter and receiver circuit 41. Voltage reference and bias circuit 37, ADC and multiplexer 39, power-on-reset circuit 45 and crystal oscillator circuit 47 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 35 in the depicted, exemplary IPG circuit 31. The patient activity sensor 27 is coupled to the IPG housing and may take the form of a piezoelectric crystal transducer as is well known in the art and its output signal is processed and used as the RCP. Sensor 27 generates electrical signals in response to sensed physical activity that are processed by activity circuit 35 and provided to digital controller/timer circuit 83. Activity circuit 35 and associated sensor 27 may correspond to the circuitry disclosed in U.S. Pat. Nos. 5,052,388 and 4,428,378. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Data transmission to and from the external programmer is accomplished by means of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 83 and A-EVENT, RV-EVENT, and LV-EVENT signals generated by sense amplifiers circuit 55, among others. The specific values of the intervals and delays timed out by digital controller/timer circuit 83 are controlled by the microcomputer circuit 33 by means of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals and the energy delivered to each ventricle.

In one embodiment, microprocessor 80 is a custom microprocessor adapted to fetch and execute instructions stored in RAM/ROM unit 82C in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 83 operates under the general control of the microcomputer 33 to control timing and other functions within the pacing circuit 21 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (i.e., either an A-RVp delay or an A-LVp delay as determined using known methods) to time-out starting from a preceding A-PACE or A-EVENT. The interval timer 83E triggers pacing stimulus delivery, and can based on one or more prior cardiac cycles (or from a data set empirically derived for a given patient).

The post-event timers 83F time out the post-ventricular time periods following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, post-ventricular time periods, and post-atrial time periods that vary with the sensor based escape interval established in response to the RCP(s) and/or with the intrinsic atrial rate.

The output amplifiers circuit 51 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 83 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers corresponding to any of those presently employed in contemporary cardiac pacemakers for atrial and ventricular pacing and sensing. As noted in the above-referenced, commonly assigned, '324 patent, it has been common in the prior art to use very high impedance P-wave and R-wave sense amplifiers to amplify the voltage difference signal which is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the atrial and ventricular sense amplifiers 55.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND_CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND_CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier, if provided, result in a LA-EVENT signal that is communicated to the digital controller/timer circuit 83. Ventricular depolarizations or R-waves in the RV-SENSE signal are sensed by a ventricular sense amplifier result in an RV-EVENT signal that is communicated to the digital controller/timer circuit 83. Similarly, ventricular depolarizations or R-waves in the LV-SENSE signal are sensed by a ventricular sense amplifier result in an LV-EVENT signal that is communicated to the digital controller/timer circuit 83. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The exemplary methods and/or devices described herein may track, or monitor, the effectiveness of pacing therapy by analyzing one or more features of a sensed morphological waveform corresponding to a paced event for one or more monitored electrical vectors of the patient's heart. As used herein, a sensed morphological waveform may correspond to a paced event by occurring within a predetermined, or selected, time period, or sensing window, (e.g., 200 milliseconds) after the delivery of pacing stimulus. The sensed morphological waveform may, e.g., result from the delivery of pacing stimulus and/or intrinsic conduction.

Figure 4:
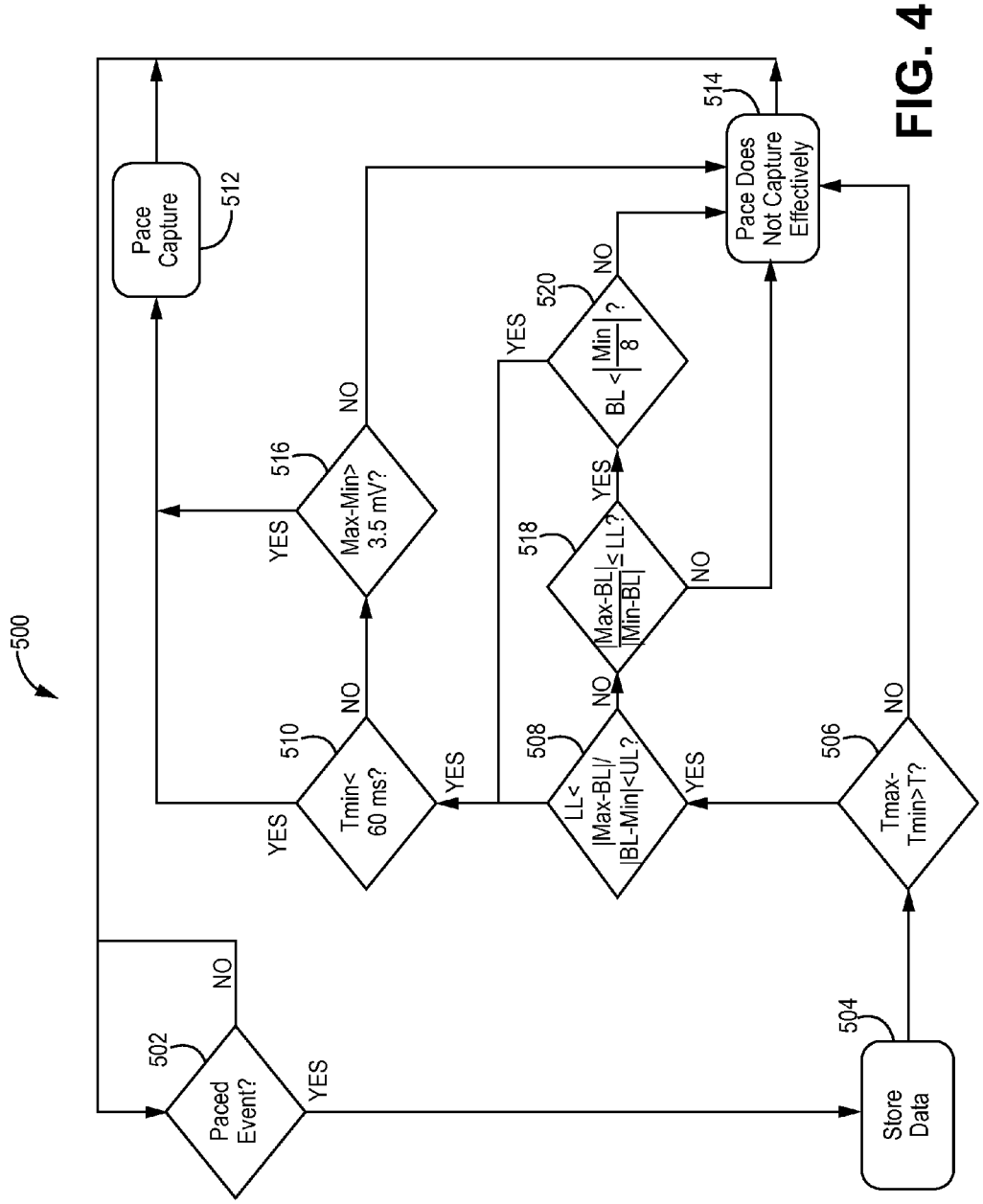
FIG. 4 is a flowchart of an exemplary method for determining whether an electrical stimuli effectively captures a ventricle.

FIG. 4 depicts a diagnostic method 500 for use in determining pacing effectiveness in CRT pacing. In particular, morphological features following delivery of a paced event are compared to absolute levels (i.e., thresholds that are not patient specific). For example, exemplary systems and methods described herein monitor one or more electrical vectors of a patient's heart during pacing therapy, analyzing whether each paced event has a predetermined level of effectiveness. In one or more embodiments, morphological features are evaluated of a LV vector-RV coil vector during LV only pacing or biventricular (BV) pacing in CRT. Exemplary LV vector-RV coiled vector can include electrode pairings such as a LV tip (e.g. electrode 46) to RV coil (e.g. electrode 62), or LV ring (e.g. electrode 54) to RV coil (e.g. electrode 62). It is advantageous to select a monitoring vector that includes the LV pacing cathode and another electrode such as a RV coil or the IMD 16 case or housing. For example, if LV pacing is occurring at the LV tip, then it is preferable to employ a monitoring vector of Lvtip-Rvcoil or Lvtip-device case.

Figure 5:
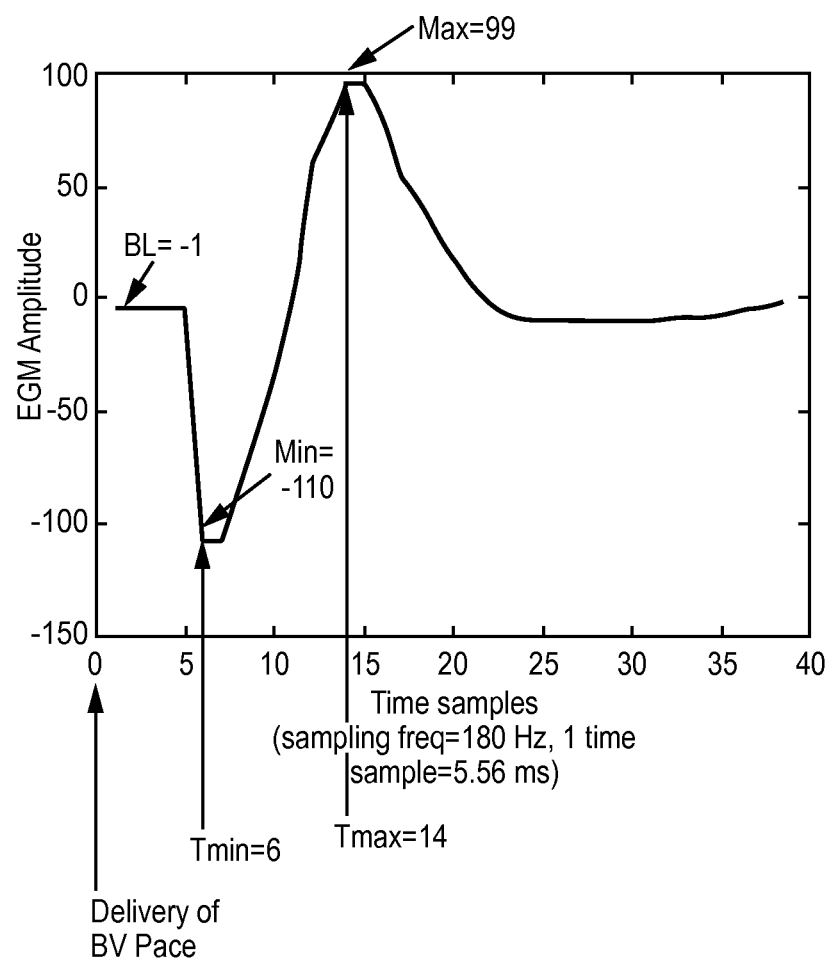
FIG. 5 graphically depicts data that supports an effective capture test depicted in flowchart of FIG. 4.

At block 502, a determination is made as to whether a current or latest ventricular event is a paced event. If the device did not deliver a paced event, the NO path is followed, returning to block 502 to continue checking for the next paced event. If a paced event has occurred, the YES path continues to optional block 504 so that the electrogram data from the monitored vector can be stored into memory. Block 504 is optional since data storage can automatically occur independently of the computer instructions set forth in method 500. Exemplary EGM data resulting from a paced event is depicted in FIG. 5. As shown, electrical stimuli (e.g. a biventricular pacing pulse) was delivered through a medical electrical lead to cardiac tissue at time=0 while the data is sampled at an exemplary sampling frequency of 180 Hz (5.56 ms per sample). Baseline data value (BL), used as a reference value, is sensed immediately before a pacing stimulus is delivered. In the example of FIG. 5, the device holds the baseline data value during a period of blanking that immediately precedes and follows the delivery of a pacing stimulus, so the BL can also be sensed during the holding period (i.e., immediately after a pacing stimulus is delivered). For example, the BL EGM amplitude is −1 and the minimum EGM amplitude is −110 where the units are equal to the least significant bit (LSB) voltage of the analog-to-digital converter (ADC). By way of illustration, if the full scale voltage range of the ADC is 8 millivolts (mV) and the ADC has a 8 bit resolution then the LSB voltage is $8*1000/(2^8-1)=31.3$ microvolts (μV). The timing of the minimum amplitude occurs at 6 time-samples (i.e., 33.4 milliseconds (ms)) from the time the pacing stimulus is initially delivered to cardiac tissue. After the delivery of the pacing stimulus, the maximum EGM amplitude is 99 and the timing of the maximum amplitude is 14 time-samples (i.e. 78.4 ms).

To determine whether a pacing stimulus effectively captures a ventricle, sensed data is evaluated according to one or more of the mathematical relationships embodied at blocks 506, 508, 510, 516, 518, and 520. At block 506, a determination is made as to whether a first condition relative to effective capture is met. The first condition, presented below, subtracts Tmin from Tmax and then determines whether the result is greater than a predetermined threshold (T) such as 30 ms. The equation for the first condition is as follows:

$$Tmax-Tmin>30 \text{ ms}$$

If Tmax−Tmin is not greater than 30 ms, then the NO path continues to block 514 in which the pacing stimulus is declared to ineffectively capture a ventricle. In contrast, if Tmax−Tmin>30 ms, the YES path continues to block 508. The data presented in FIG. 5 provides an example of this condition being satisfied since Tmax−Tmin is equal to 78.4-33.4 ms which equals 45 ms. At block 508, a determination is made as to whether a second condition is met. The equation for the second condition is as follows:

$$LL<|Max-BL|/|BL-Min|<UL$$

The lower limit (LL) and upper limit (UL) are associated with upper and lower ratio limits, respectively, of a morphological feature. Exemplary LL can be 0.2 with a range of 0.1 to 0.33 and exemplary UL can be 5.0 with a range of 3.0 to 10.0. Preferably, LL is set at 0.125 and the UL is set at 8.0.

The maximum value (Max) and the minimum value (Min) are associated with a particular EGM morphological feature such as amplitude. The ratio, |Max−BL|/|BL−Min|, includes the absolute value of Max−BL which is divided by the absolute value of BL−Min. If the second condition at block 508 is not satisfied, then the NO path continues to block 518 in which a determination is made as to whether (|Max−BL|/|Min−BL|) LL. If (|Max−BL|/|Min−BL|)≤LL is not met, then the NO path continues to block 514 and the ventricular pace stimuli is declared not to evoke effective capture of the ventricle. In contrast, the YES path from block 518 continues to block 520 in which a determination is made as to whether BL<|Min/8|. If BL is not less than |Min/8|, the NO path from block 520 continues to block 514 in which the electrical stimuli is declared to ineffectively capture the ventricle. If BL is less than |Min/8|, then the YES path continues to optional block 510.

The YES path from block 508 also continues to block 510 which determines whether Tmin is less than a preselected value such as 60 ms. The preselected value can be any value between 40 ms-80 ms. If Tmin is not less than 60 ms, then the NO path continues to optional block 516 in which another determination is made as to whether Max-Min is greater than 3.5 mV. If Max-Min is greater than 3.5 mV, effective capture exists and the YES path continues to block 512 in which the ventricular stimulus is declared to capture the ventricle. The NO path from block 516 continues to block 514 in which a determination is made that ventricular stimulus is determined not to effectively capture a ventricle.

Returning to block 510, if Tmin is less than 60 ms, then the YES path continues to block 512 in which effective capture is declared. Every time effective capture is declared at block 512, an effective capture counter is incremented by 1. The effective capture counter is maintained and updated continuously during effective capture monitoring. Effective capture monitoring determines whether pacing stimulus is effective or ineffective. Effective capture monitoring tracks responses from cardiac tissue during pacing therapy.

Effective capture monitoring may be performed continuously or, more preferably, performed periodically (e.g. 100 beats/hour (hr), daily etc.) in order to conserve battery life. Preferably, effective capture monitoring is performed 100 beats per hour and consists of normal pace timings (not the ideal timing conditions of ECT). The effective capture monitoring (i.e. 100 beats per hour) is reported to the user as a % of effective capture beats. The user can apply any choice of threshold for concern (e.g. 90%, etc.).

After a period of monitoring, a metric of effective capture can be computed by dividing the effective capture counter by the total number of paced beats. The method then returns to monitoring for the next paced event at block 502.

Morphological features are parsed from an EGM and are used to determine whether pacing is effectively capturing a ventricle. Exemplary morphological features include maximum value (Max), timing of maximum value (Tmax), minimum value (Min), timing of minimum value (Tmin), baseline value (BL) of the EGM amplitude at the time at which pace was delivered. The morphological features are evaluated within a time-window of pre-specified width (i.e. 200 ms) starting at the time of delivery of pacing.

To determine if effective LV capture can occur under ideal conditions, an effective capture test (ECT) is performed periodically (e.g. daily, etc.), upon the direction of a user (e.g. while the patient sleeps such as at night time), or in response to consistent observation of ineffective capture. Generally, ideal conditions relate to delivering a pacing stimulus at an adequate amplitude and time.

The result of the ECT can be used to explain reasons for the observation of ineffective capture throughout the day. For example, if a left ventricular lead is dislodged, if scar tissue develops at the location of LV pacing, or if BV pacing includes substantial pre-excitation of the RV, it may not be possible to obtain effective LV capture even under ideal conditions.

The ECT test can be performed for LV only pacing or BV pacing. The manner in which the ECT is performed depends upon whether the patient is experiencing atrial fibrillation (AF). AF generally results in switching of pacing behavior to a pacing mode that does not track atrial activation (e.g., DDI, DDIR, WI, or VVIR pacing modes). When not in AF, the device generally is operating in a pacing mode that tracks atrial activation, such that SAV and PAV are relevant pacing timing parameters. For example, if the patient is not in AF, LV-only pacing employs a very short PAV (e.g. 10 ms) or SAV (e.g. 10 ms). Alternatively, if the patient is experiencing AF, LV-only pacing employs an overdrive rate. Test beats (e.g. 5 test beats, etc.) are delivered to a ventricle to determine whether the ventricle was effectively captured in accordance with the criteria presented in FIG. 4 and the accompanying text. If, for example, 75% of the tested beats such as 4 of 5 beats are effectively captured, the ECT is passed for that day. Passing the ECT for that day means that effective capture is at least possible under ideal conditions. Effective capture by electrical stimuli occurs when at least 75% of the number of tested days (i.e., 31 out of 40 days) passed the ECT.

The BV test follows the LV test. For the BV test, a very short PAV or SAV is used along with the currently programmed W delay if the patient is not in AF, and an overdrive rate is employed if the patient is in AF. Again, 5 test beats are delivered with BV pacing, and 4 of 5 must pass effective LV capture. LV paced beat or BV paced beat is deemed to provide effective capture if the morphological features satisfy the effective capture test (ECT). The ECT can comprise one, two or three of the following relationships:

$$Tmax - Tmin > 30 \text{ ms} \quad (1)$$

$$0.2 < |Max-BL|/|BL-Min| < 5 \text{ or } (|Max-BL|/|Min-BL| \le LL \text{ and } BL < |Min/8|) \text{ and} \quad (2)$$

$$Tmin < 60 \text{ ms or } Max-Min > 3.5 \text{ mV} \quad (3)$$

All timing parameters are measured from the time at which the pace is delivered.

Figure 6:
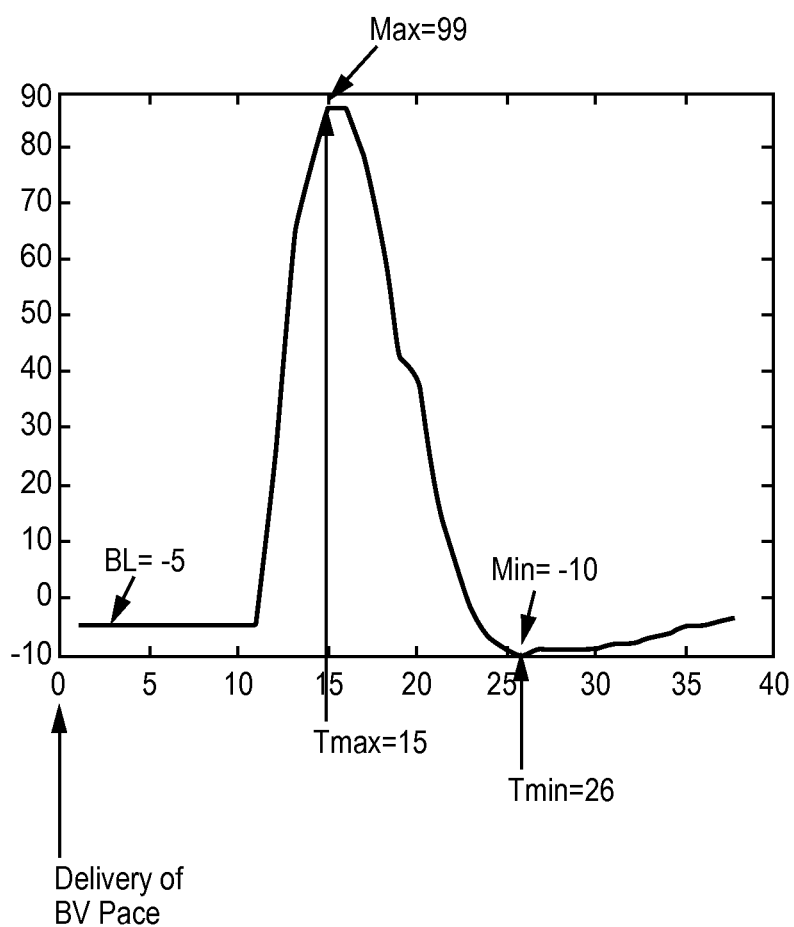
FIG. 6 graphically depicts data, used in the flowchart of FIG. 4, in which effective capture has not occurred.
Figure 7:
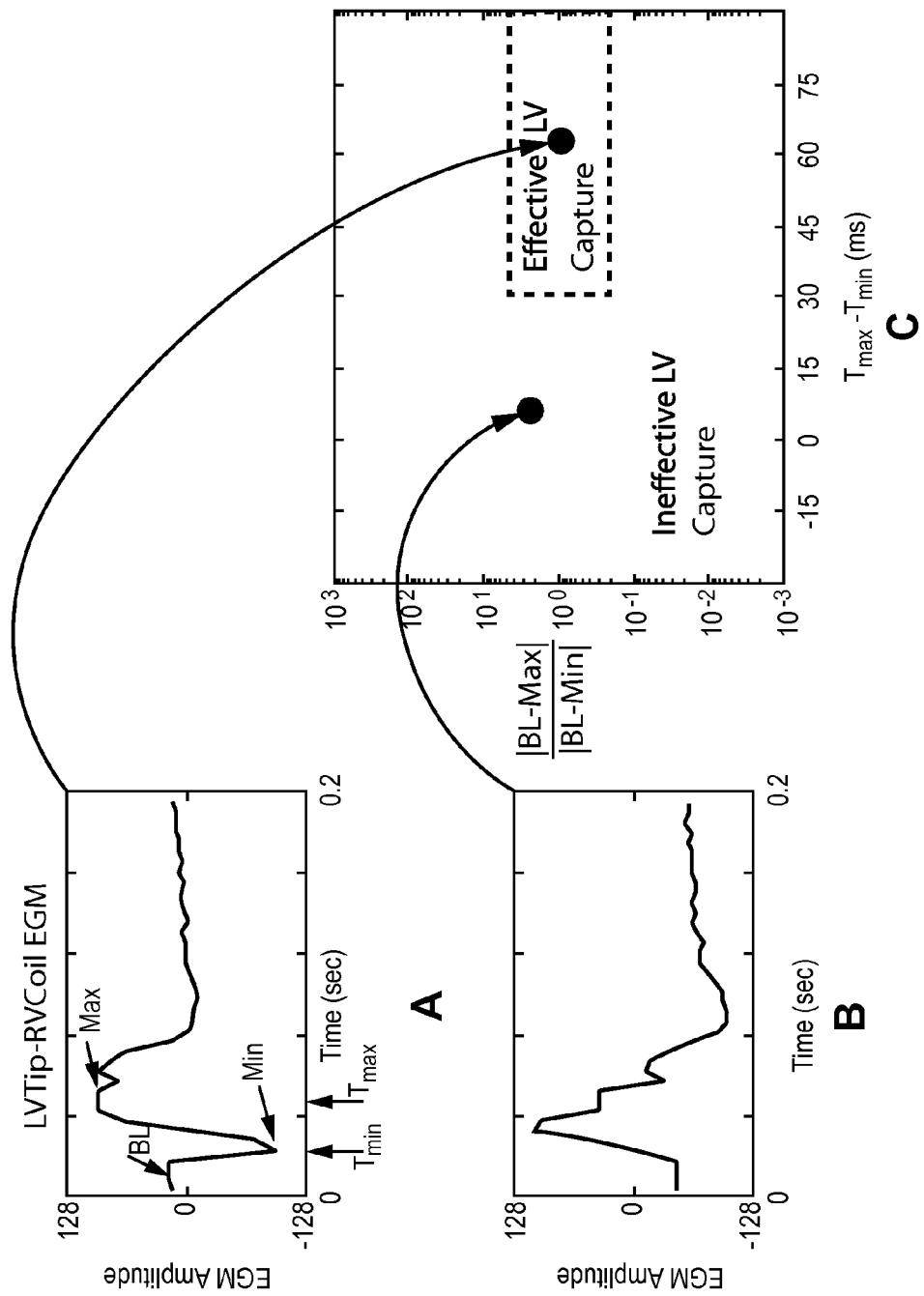
FIGS. 7A-7C graphically depicts data that supports an effective capture test depicted in flowchart of FIG. 4.

Table 1 summarizes exemplary method 500 diagnostic data. The two different examples of diagnostic data, shown in FIGS. 5 and 6, depict R waves from the QRS complex of the cardiac cycle. The R wave, a depolarization of the ventricles, generally has an amplitude greater than any other wave of the cardiac cycle and is characterized by a rapid deviation from and return toward baseline.

FIG. 5 shows a negative deflection preceding a positive deflection while FIG. 6 depicts a positive deflection preceding a negative deflection of the signal. A negative deflection occurs when a curve falls below the base line. A negative deflection indicates that a recorded far field wave has traveled away from one of the electrodes on a lead. In contrast, a positive deflection occurs when a curve rises above the base line as depicted in FIG. 6. The positive deflection means the recorded far field wave has traveled toward the electrode.

Turning now to the application of the ECT criteria, the pacing data presented in FIG. 5 delivered effective pacing to capture the ventricle since blocks 506, 508 and 510 of FIG. 4 were successfully passed. Pacing data presented in FIG. 6 ineffectively captured the ventricle since Tmax−Tmin is not greater than 30 ms as to block 506. Table 1 lists the ECT criteria along with each result for the pacing data presented in FIGS. 5 and 6.

TABLE 1

Summary of two different pacing effectiveness examples.

| Parameter or condition | Example 1-FIG. 5 | Example 2-FIG. 6 |
|---|---|---|
| Tmax | 78.4 ms | 83.4 ms |
| Tmin | 33.4 ms | 144.6 ms |
| BL | −1 | −5 |
| Min | −110 | −10 |
| Max | 99 | 88 |
| Tmax − Tmin > 30 | 78.4 − 33.4 > 0 | 83.4-144.6 is less than zero; therefore, pacing stimulus does not effectively capture |
| 0.2 < \|Max − BL\|/ \|BL − Min\| < 5 | 0.2 < \|.99\| < 5 | Does not test for this condition |
| Tmin < 60 ms | 33.4 ms < 60 ms | Does not test for this condition |
| Effectively pacing? | Yes | No |

The conditions for classifying a paced beat as effective or ineffective capture can be conveniently displayed as a two-dimensional scatter plot. FIGS. 7A-7C support conditions found in the flow chart of FIG. 4. FIGS. 7A-7B depict a LVtip-RV coil EGM. The EGM amplitude, along the Y-axis, extends from −128 to 128 while the X-axis extends from 0 to 0.2 seconds. Data such as BL, Min, Max, Tmin, Tmax are shown for each stimuli and are compared to the criteria for effective capture. The data is then mapped onto the scatter plot of FIG. 7C. As shown, effective capture exists within the boxed area from the stimuli delivered from FIG. 7A while ineffective capture exists outside of the boxed area as evoked from the electrical stimuli delivered from FIG. 7B. Note that the third criterion for effective capture (Tmin<60 ms or Max−Min>3.5 mV) is not included in this graphical depiction and is not required for effective capture determination in one or more other embodiments.

Figure 8:
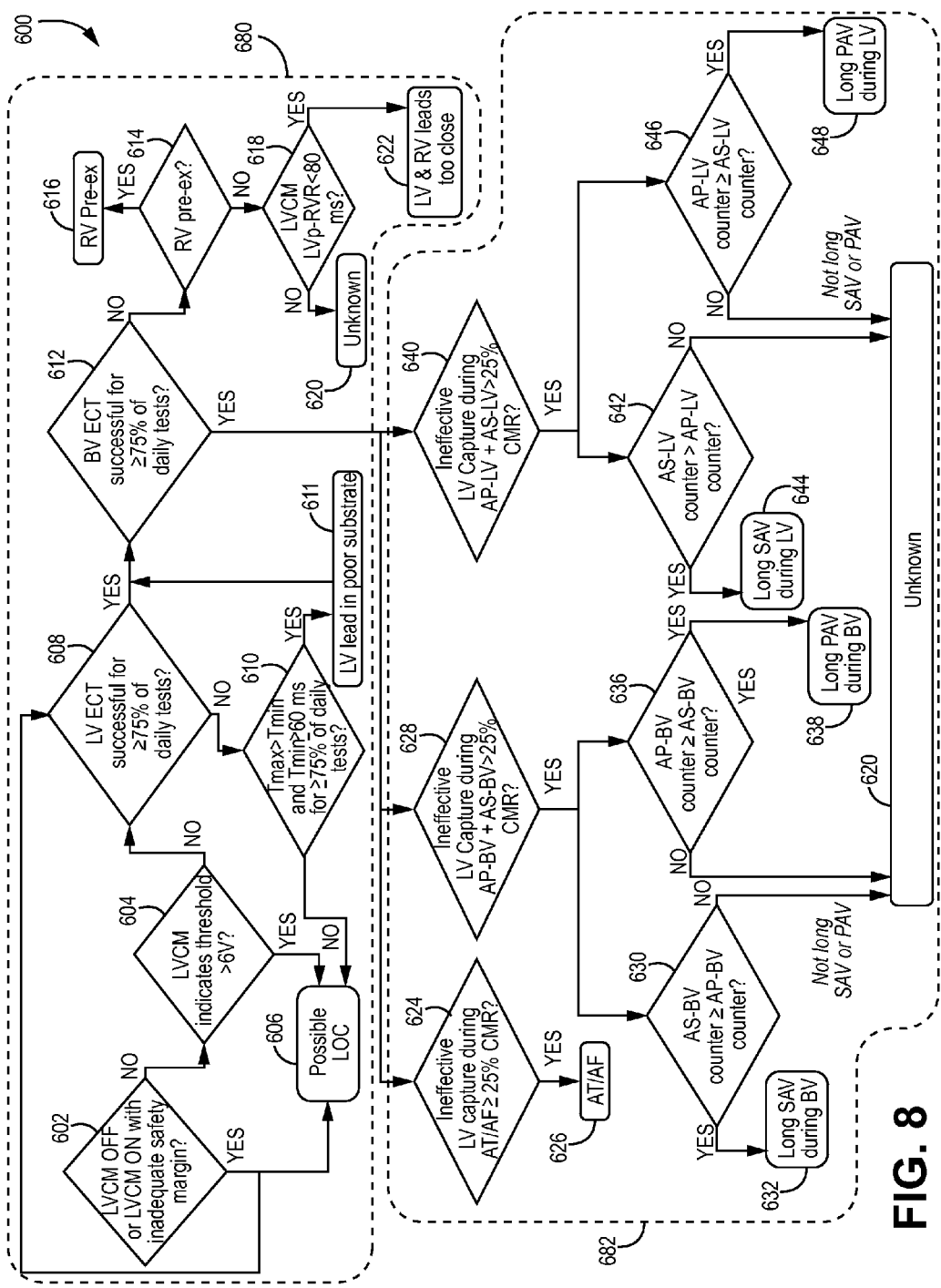
FIG. 8 is a flowchart of an exemplary diagnostic method for use in explaining electrical stimulus that is ineffectively capturing a ventricle.

After ineffective capture has been determined to exist for a substantial portion of paced beats over a period of follow-up and diagnostic data has been collected by an IMD 16, diagnostic method 600 shown in FIG. 8 presents diagnostic classifications that explain the reason for the ineffective capture. Ineffective capture can result from insufficient energy delivery to the ventricle, a poor pacing substrate (i.e., ventricular tissue that is inexcitable), or poor pace timing. The diagnostic method advantageously employs the results from left ventricular capture management (e.g. left ventricular capture management (LVCM) etc.) to determine if the delivered energy is sufficient for effective capture. LVCM is a set of computer instructions, executed by the processor, that automatically monitors and, if applicable, adjusts LV output to attempt to secure ventricular capture. LVCM can minimize LV output that is delivered to capture the left ventricle, while enforcing a safety margin of amplitude over the required amplitude for ventricular capture, in order to reduce undesirable effects of electrical stimulation such as phrenic nerve stimulation. LVCM can also indicate that left ventricular capture cannot be obtained, even with high energy deliveries.

Diagnostic method 600 uses daily test results 680 (i.e. using the ECT) and CMR results 682 to determine a diagnosis. The diagnostic method begins at block 602 in which at least one of two different determinations can be made such that LVCM is OFF or is ON with an ineffective safety margin (i.e., a safety margin less than a predetermined amount of volts (e.g. less than 0.5 volts, less than 1 volt etc.).

The NO path from block 602 continues to block 604 in which a determination is made as to whether LVCM threshold on output is greater than a predetermined level (e.g. 6 volts, etc.). If the LVCM threshold is greater than 6 volts, then the YES path continues to block 606 and possible loss-of-capture (LOC) is indicated as a diagnostic classification. A LOC signal is optionally generated and sent to a graphical user interface (GUI) of a programmer for the user.

Returning to block 602, if either of the listed conditions are present, the diagnostic method then performs two different parallel determinations. One YES path continues to block 606 which indicates possible LOC. Another YES path from block 602 continues to block 608 to seek additional reason(s) for ineffective capture. At block 608, if less than or equal to 75% of the periodic (e.g. daily) LV-only ECT tests pass (i.e., the "NO" path), then effective capture cannot be achieved under ideal timing conditions. This occurs if either the delivered pacing energy is insufficient (i.e., loss of capture, block 606) or if the lead is pacing into generally inexcitable tissue (i.e., poor pacing substrate, block 611). Block 610 separates these two conditions. At block 610, determinations are made as to whether Tmax is greater than Tmin and also whether Tmin is greater than or equal to 60 ms for greater than or equal to 75% of the daily tests. If both conditions are met, then the YES path continues to block 611 and the LV lead is determined to be located in a poor substrate (e.g. scar tissue etc.). The determination that the LV lead is located in a poor substrate is then displayed on a GUI of the programmer to a user. In contrast, if Tmax is not greater than Tmin or Tmin is less than 60 ms for greater than or equal to 75% of the tests, then the NO path continues to block 606, which indicates a possible LOC.

Returning to block 608, if the determination is made that LV-only ECT were successful greater than 75% of the days when a test was conducted, then the YES path is followed to block 612. At block 612, a determination is made as to whether BV ECT were successful for greater than or equal 75% of the days when a test is conducted. If this BV ECT condition is not met, then the NO path continues to block 614. At block 614, a determination is made as to whether RV is pre-excited. RV is pre-excited when the RV pace is delivered before the LV pace, i.e., RV−LV>0. If RV is programmed to pre-excitation, then the YES path continues to block 616 in which RV pre-excitation is declared. The processor generates a signal causing RV pre-excitation to be displayed on a GUI associated with the programmer. RV pre-excitation can be easily addressed through an automated adjustment of delivering the paced event. Alternatively, if RV−LV≤0, then the NO path continues to block 618 in which a determination is made as to whether the time between premature delivery of an LV pace (LVp) to sensing of ventricular activation by a right ventricular lead (RVR, thus forming an "LVp−RVR" conduction time) is less than 80 ms. If LVp−RVR is less than 80 ms during pacing at a very short A-V delay, the LV and RV leads are in close physical proximity to one another.

If LVp−RVR is not less than 80 ms, then at block 620, the term "unknown" is displayed to the user on a GUI associated with the programmer. Further evaluation of the "unknown" condition is performed by other means. For example, the user may need to obtain and evaluate other data related to the patient. In contrast, if LVp−RVR is less than 80 ms, then at block 622, the "LV and RV leads are too close" is displayed to the user on a GUI associated with the programmer. The user may then consider physical or electrical repositioning of one or both the LV lead and/or the RV lead. Electrical repositioning means choosing a different electrode from which to pace.

Returning to block 612, if the data successfully passes the BV ECT, then the YES path continues to perform parallel determinations, using effective capture monitoring results (CMR), at blocks 624, 628 and 640. CMR is data sensed from the cardiac tissue in response to pacing therapy during normal pace timing conditions. CMR involves continuous tracking or monitoring of beats for the purpose of reporting how much effective capture is occurring, which, in turn, indicates CRT effectiveness.

Skilled artisans will appreciate that multiple ways exist for tracking ineffective LV capture that occurred during (1) AF, (2) AS-BV, (3) AP-BV, (4) AS-LV, or (5) AP-LV. For example, when an ineffective LV capture beat occurs, counters can be used to track when that beat occurred during a particular condition such as during (1) AF, (2) AS-BV, (3) AP-BV, (4) AS-LV, or (5) AP-LV. At block 624, a determination is made as to whether greater than or equal to 25% CMR had ineffective LV capture that occurred during atrial tachycardia/fibrillation (AT/AF). If greater than or equal to 25% CMR indicates ineffective LV capture that occurred during AT/AF, then the YES path continues to block 626 in which AT/AF is indicated to be present. An AT/AF diagnostic signal is optionally generated and displayed on the GUI such as the exemplary GUI shown in FIG. 10. As noted, the effective ventricular pacing (VP) is merely 65% which is far below the desired level of 90% or greater effective VP. Other valuable data such as battery life, alerts (e.g. invalid data, electrical reset, RRT and low battery voltage are also included).

At block 628, a determination is made as to whether greater than or equal to 25% CMR indicates ineffective LV capture occurred during atrial pace (AP)-BV or atrial sense (AS)-BV. The YES path continues to block 630 in which a determination is made as to whether more ineffective LV capture occurred during AS-BV or AP-BV. The YES path continues to block 632 in which long SAV during BV is determined to exist. The NO path from block 630 continues to block 620 which indicates an "unknown" explanation thereby possibly prompting further evaluation by the user.

Figure 11:
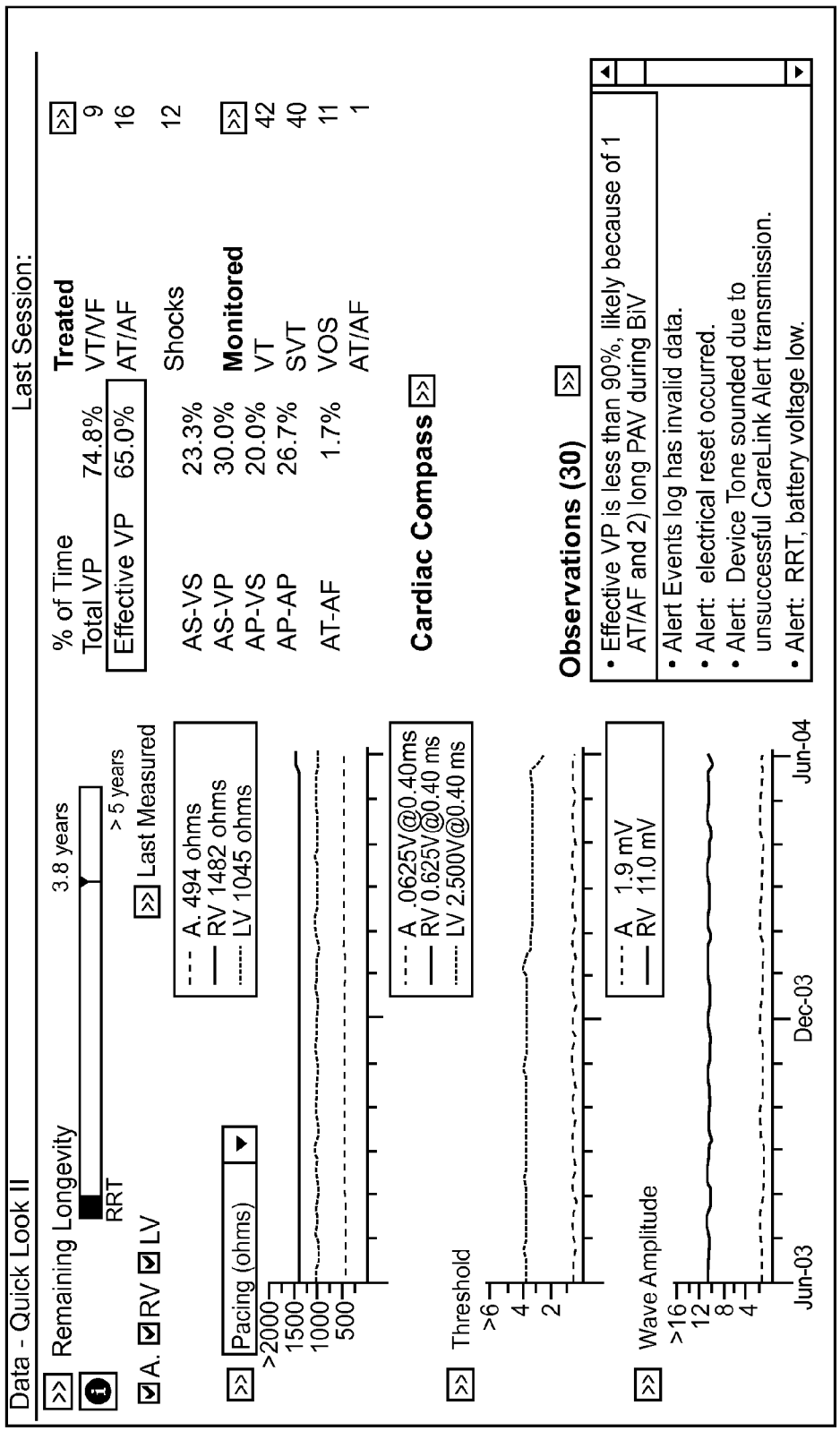
FIG. 11 is a graphical display of data obtained during evaluation of capture ineffectiveness due to atrial tachycardia/fibrillation and a long paced atrioventricular delay (PAV) during biventricular pacing.
Figure 12:
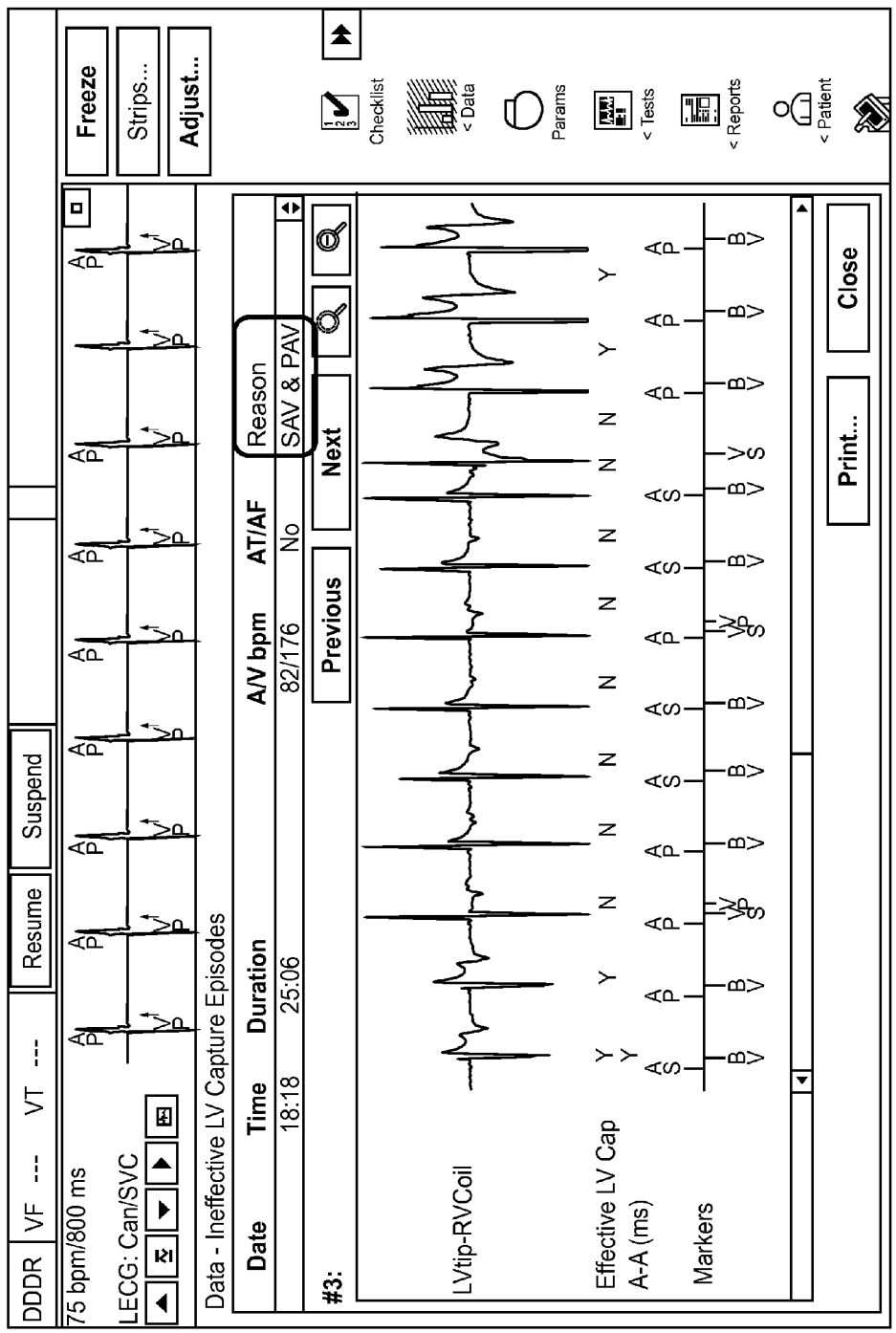
FIG. 12 depicts a graphical user interface of a programmer that explains ineffective capture of a ventricle is due to sensed atrioventricular delay (SAV) and PAV.

At block 636, a determination is made as to whether more ineffective LV capture occurred during AP-BV than during AS-BV. If the number of ineffective LV capture beats during AP-BVs is greater than or equal to the number of ineffective LV capture beats during AS-BVs, the YES path continues to block 638 in which a long PAV during BV is determined to exist. FIG. 11 is an exemplary GUI that shows valuable data to the user. For example, effective VP is 65% which is less than the desired 90% or greater effective VP. Additionally, the GUI indicates that the ineffective pacing is likely due to (1) AT/AF and (2) long PAV during BV. While adjustment can be automatically made to address the PAV that is too long, the user can optionally control any adjustment through manual input.

Returning to block 618, the NO path continues to block 620 in which an unknown result is displayed, which may prompt the user to continue to seek additional data. At block 640, a determination is made as to whether ineffective LV capture is occurring during AP-LV+AS-LV>25% CMR, as described above. At block 642, if AS-LV counter >AP-LV counter, then the YES path continues to block 644 in which a GUI displays that a long sensed atrioventricular delay (SAV) is occurring during LV.

If the AS-LV counter is less than or equal to AP-LV counter at block 642, then the NO path continues to block 620 which indicates an "unknown" explanation.

At block 646, a determination is made as to whether AP-LV counter is greater than or equal to a AS-LV counter. If so, then the YES path continues to block 648, which indicates that a long paced atrioventricular delay (PAV) during BV. The long PAV during LV is then displayed on a GUI. Alternatively, if AP-LV counter is less than or less than a AS-LV counter.

Figure 9:
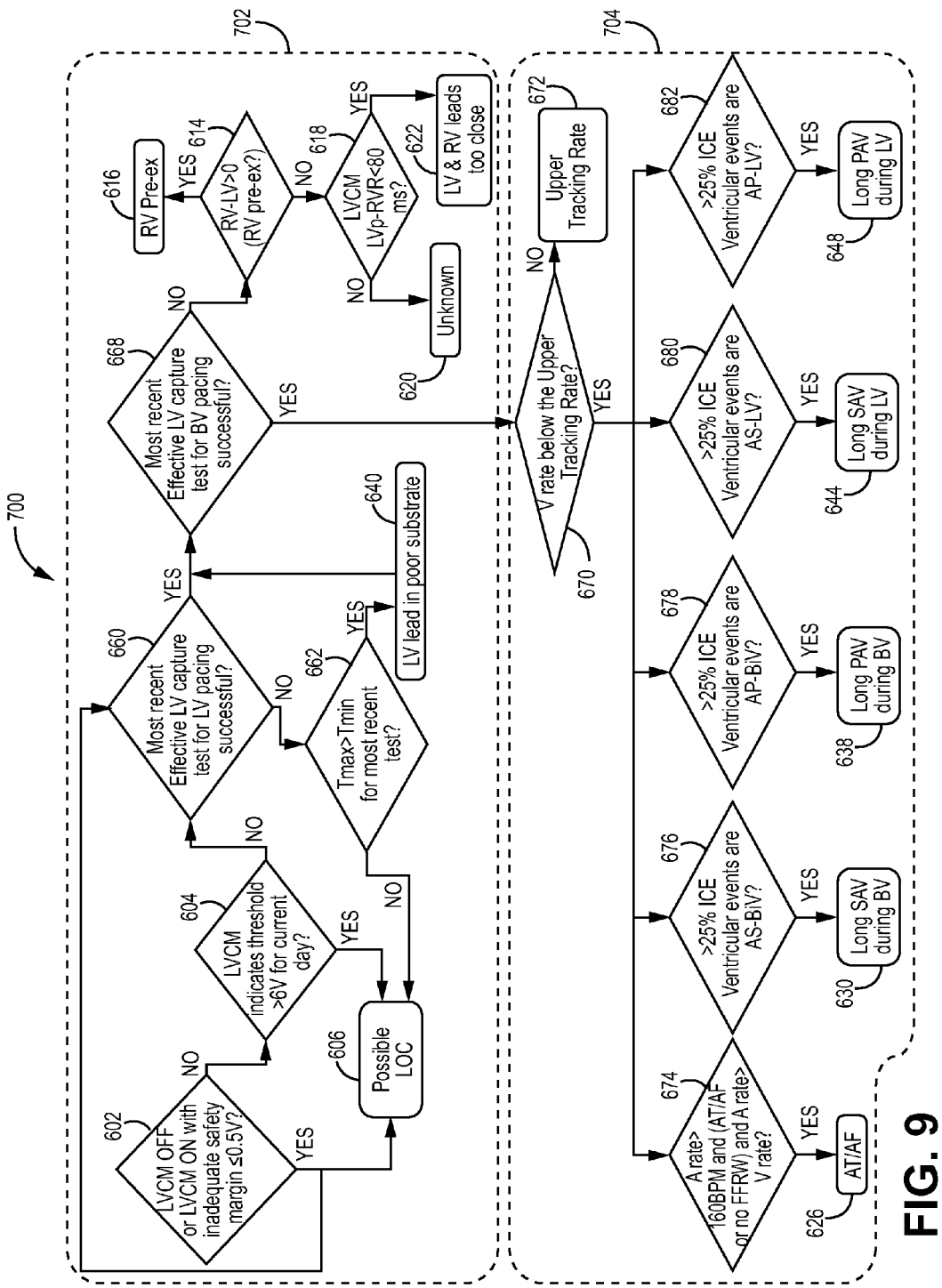
FIG. 9 is a flowchart of yet another exemplary diagnostic method for use in explaining electrical stimulus that is ineffectively capturing a ventricle.

An additional means of explaining reasons for loss of effective capture is storage of episodes with consistent runs of ineffective capture beats. These "ineffective capture episodes" (ICE) are acquired by the device when a consecutive number of CRT beats resulted in ineffective capture. A typical threshold employed by the device could be 10 consecutive CRT beats that result in ineffective capture. The ineffective capture episodes can be displayed (e.g. FIG. 12) to the user for interpretation and appropriate corrective action. An automated algorithm to explain the reason for each ineffective capture episode would facilitate this interpretation and corrective action. FIG. 9 is a flow chart of an exemplary diagnostic method 700 for explaining ineffective capture episodes. Method 700 is the same as method 600 except as modified below. Diagnostic method 600 relies on daily test results 702 (i.e., through employing the ECT) and CMR results 704 to determine a diagnosis. At block 660, a determination as made as to whether the most recent or latest ECT for LV pacing is successful. If there is no effective LV capture, the NO path continues to block 662 and block 606 where LOC is declared as shown in FIG. 9. In contrast, a recent ECT allows the YES path to continue to block 668 in which a determination is made as to whether the most recent effective capture test was performed for biventricular pacing. At block 670, a determination is made as to whether the V rate is below a preselected upper tracking rate. An upper tracking rate is programmed by the user to be the highest sinus tachycardia rate that the device will track with ventricular pacing. A common value for the upper tracking rate is 120 BPM. If the ventricular rate (V rate) is not below a preselected upper tracking rate, then the NO path continues to block 672 in which the upper tracking rate is declared as requiring adjustment. If the V rate is below a preselected upper tracking rate, then the NO path continues to a set of parallel determinations as set forth relative to blocks 674, 676, 678, 680, and 682.

At block 674, a series of determinations are made. One determination is whether the A rate is greater than 160 beats per minute (BPM). Another determination is whether AT/AF is present or whether no far-field R-wave (FFRW) is present. Yet another determination is whether the A rate is greater than the V rate. If all three conditions are true, then the YES path continues to block 626. At block 676, a determination is made as to whether greater than 25% ineffective capture episode (ICE) ventricular events are classified as AS-biventricular pacing. Therefore, out of 10 consecutive beats without effective LV capture, a further determination is made as how many beats were AS-BV, how many beats were AP-BV, etc.

Returning to block 636, the YES path continues to block 638 in which a long PAV during BV is declared.

At block 678, a determination is made as to whether greater than 25% ICE ventricular events are AP-BV. If so, the YES path continues to block 638 in which a long PAV during BV is declared.

At block 680, a determination is made as to whether greater than 25% ICE ventricular events are AS-LV. If so, the YES path continues to block 644 in which a long SAV during LV is declared. At block 682, a determination is made as to whether greater than 25% ICE Ventricular events are AP-LV. If so, the YES path continues to block 648 in which a long PAV during LV is declared.

Figure 13:
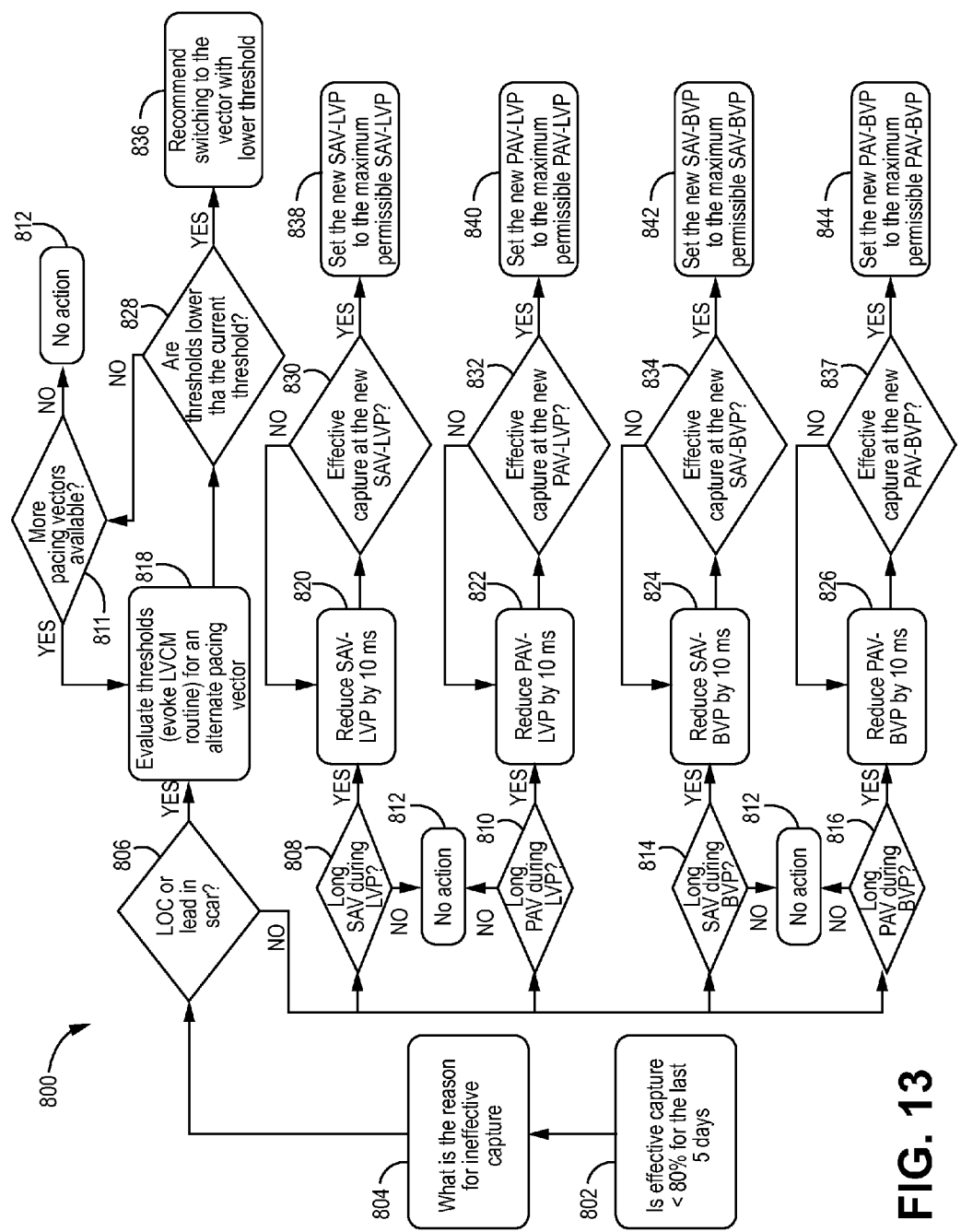
FIG. 13 is a flowchart of an exemplary method that automatically adjusts settings on an implantable medical device to more effectively capture a ventricle.

FIG. 13 is a flow chart of method 800 in which one or more automated actions are implemented by IMD 16 in response to determining ineffective capture of a ventricle. Ineffective capture is due to a diagnostic classification described relative to FIGS. 8-9. Exemplary automated actions include switching pacing vectors and/or modifying the SAV/PAV. Automated actions are only implemented if there is a persistent problem with ineffective capture over a period time (e.g. several days, less than a week etc). For example, if ineffective capture persists over a week due to a LOC or a lead is located in scar tissue, alternate pacing vectors may be tested for lower thresholds and the IMD 16 can automatically change the pacing vector if other vectors are available.

If the reason for ineffective pacing is PAV or SAV related, the IMD 16 initiates an automated action in which PAV or SAV are iteratively reduced by small decrements (e.g. 10 ms or less) and effective capture is then evaluated during delivery of therapy at the reduced PAV/SAV. If effective capture is determined to exist at the reduced PAV/SAV, the latest PAV/SAV is set as the maximum permissible PAV/SAV during subsequent delivery of therapy. For example, if the algorithm for IMD 16 performs an automatic calculation of SAV/PAV and determines a value of PAV/SAV that is less than this value, the IMD 16 calculated SAV/PAV is used for therapy. However, if the IMD 16 calculated SAV/PAV is a higher value than the SAV/PAV set in IMD 16, the newly calculated SAV/PAV is rejected in favor of the maximum permissible PAV/SAV.

Skilled artisans appreciate that the data register for the maximum PAV/SAV can be automatically cleared after a predetermined timeout period (e.g., 1-10 minutes etc.) and the process is repeated for obtaining the maximum PAV/SAV. Clearing the maximum PAV/SAV data register after a timeout period can ensure that the maximum PAV/SAV can be used to accommodate changing physiological conditions.

Automated action method 800 begins at block 802 in which a determination is made as to whether effective capture is less than a predetermined threshold for the latest period of time (e.g. 5 days). Skilled artisans appreciate that an exemplary predetermined threshold can be set at 80% and could range from, for example, 98% to 50%. Additionally, while the latest period of time could be set at 5 days, it should be appreciated that the latest period of time could range from 1 hour to 14 days. At block 804, the reason for ineffective capture is accessed by processor 80 from memory 82, which was previously determined through FIGS. 8-9. At block 806, a determination is made as to whether LOC or a lead is located in scar tissue. The YES path from block 806 continues to block 818. At block 818, thresholds of alternative pacing vectors are evaluated via the LVCM routine or other capture threshold determination means. At block 828, a determination is made as to whether one or more thresholds is lower than the current threshold. If the threshold is lower than the current threshold, the YES path continues to block 836. A recommendation can be automatically implemented by IMD 16 to switch to the vector with a lower threshold. Returning to block 828, the NO path continues to block 811 to allow a determination to be made as to whether more pacing vectors are available. If there are no other pacing vectors available, the NO path continues to block 812 and no action is taken. In contrast, if more pacing vectors are available, then the YES path continues from block 811 to block 818 and thresholds are again evaluated to locate a preferred pacing vector to attain effective capture.

The NO path from block 806 continues to a series of parallel determinations that are made at blocks 808, 810, 814, and 816. At block 808, a determination is made as to whether a long SAV exists during LVp. If not, no action is performed at block 812. If long SAV is present during LVp, then the YES path continues from block 808 to block 820 in which SAV-LVp is reduced or decremented. The present value for SAV-LVp is decremented by a preselected value (e.g. 10 ms or less). At block 830, a determination is made as to whether effective capture is attained at the new SAV-LVp. If effective capture is attained, the new SAV-LVp is set as the maximum permissible SAV-LVp at block 838. In contrast, if effective capture is not attained, then the path continues from block 830 to block 820 in which the SAV-LVp is again decremented and evaluated for effective capture.

At block 810, a determination is made as to whether a long PAV is occurring during LV pacing. The NO path from block 810 continues to block 812 in which no action is implemented. The YES path continues to block 822 in which the PAV-LVp is automatically reduced. A reduction in the PAV-LVp is preferably 10 ms or less. Thereafter, a determination is made as to whether effective capture exists through implementation of the updated or latest PAV-LVp by IMD 16 at block 832. If effective capture is not occurring with the updated or latest PAV-LVp, the NO path from block 832 returns to block 822 which again reduces the PAV-LVp and then rechecks whether effective capture is being achieved using the latest PAV-LVp. Returning to block 832, once a determination is made that the latest PAV-LVp achieves effective capture, the latest PAV-LVp is set as the maximum permissible PAV-LVp at block 840.

Returning to another NO path extending from block 806, a determination is made as to whether a long SAV is present during BV pacing at block 814. At block 824, the SAV-BV pacing is reduced by about 10 ms or less from the latest SAV-BV pacing setting. Thereafter, a determination is made as to whether effective capture exists through implementation of the updated or latest SAV-BVp by IMD 16 at block 834. If effective capture is not occurring with the updated or latest SAV-BVp, the NO path from block 834 returns to block 824 which again reduces the SAV-BVp and then rechecks whether effective capture is being achieved using the latest SAV-BVp. Returning to block 834, once a determination is made that the latest SAV-BVp achieves effective capture, the latest SAV-BVp is set as the maximum permissible SAV-BVp at block 842.

Returning to yet another NO path that extends from block 806, a determination is made as to whether a long PAV is present during BV pacing at block 816. At block 826, the PAV-BV pacing is reduced by about 10 ms or less from the latest PAV-BV pacing.

Thereafter, a determination is made at block 837 as to whether effective capture exists through implementation of the updated or latest PAV-BVp by IMD 16. If effective capture is not occurring with the updated or latest PAV-BVp, the NO path from block 836 returns to block 826 which again reduces the PAV-BVp and then rechecks whether effective capture is being achieved using the latest PAV-BVp. Returning to block 836, once a determination is made that the latest PAV-BVp achieves effective capture, the latest PAV-BVp is set as the maximum permissible PAV-BVp at block 844.

Figure 14:
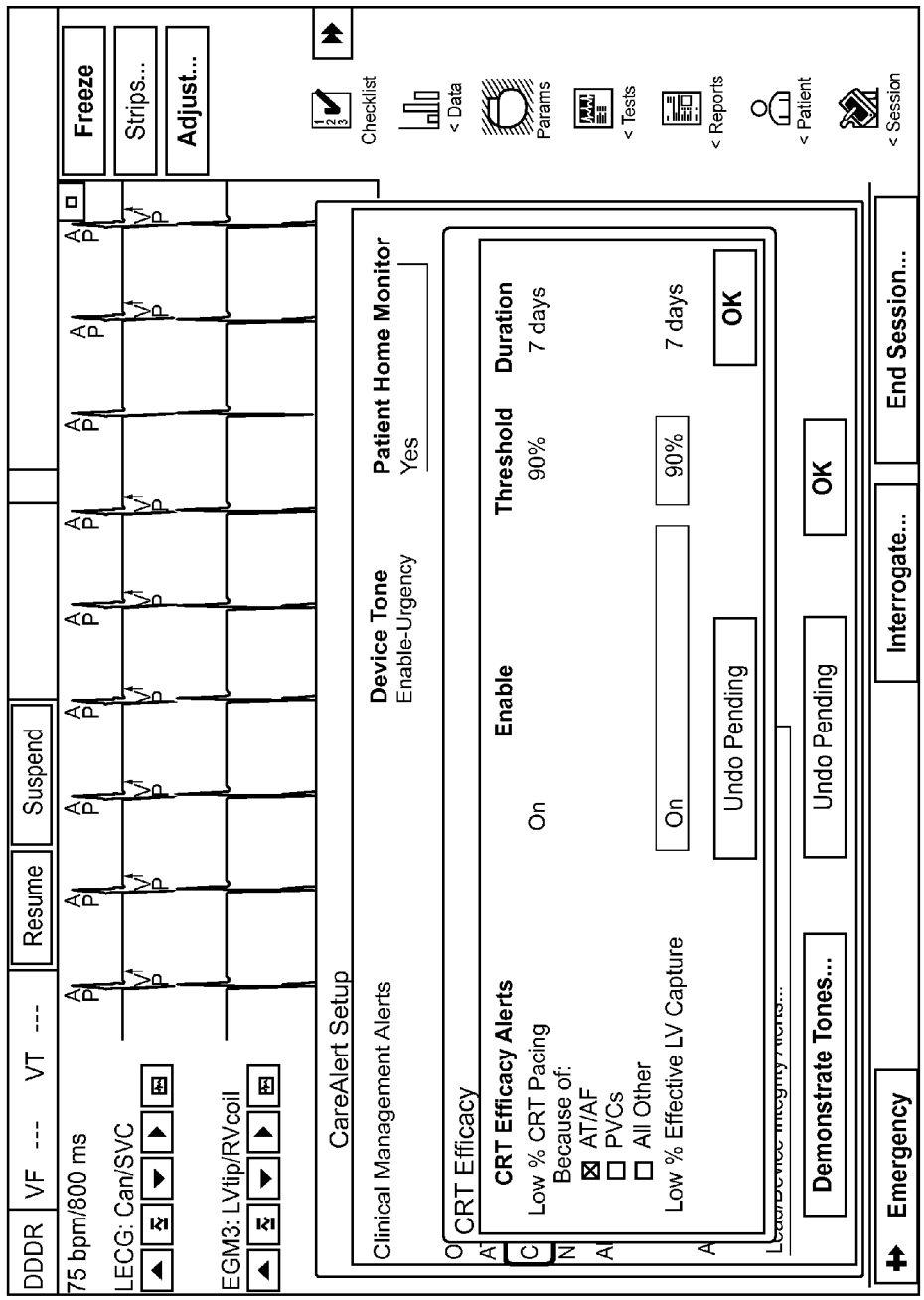
FIG. 14 is an exemplary graphical user interface that alerts a physician as to a condition in a patient.
Figure 15:
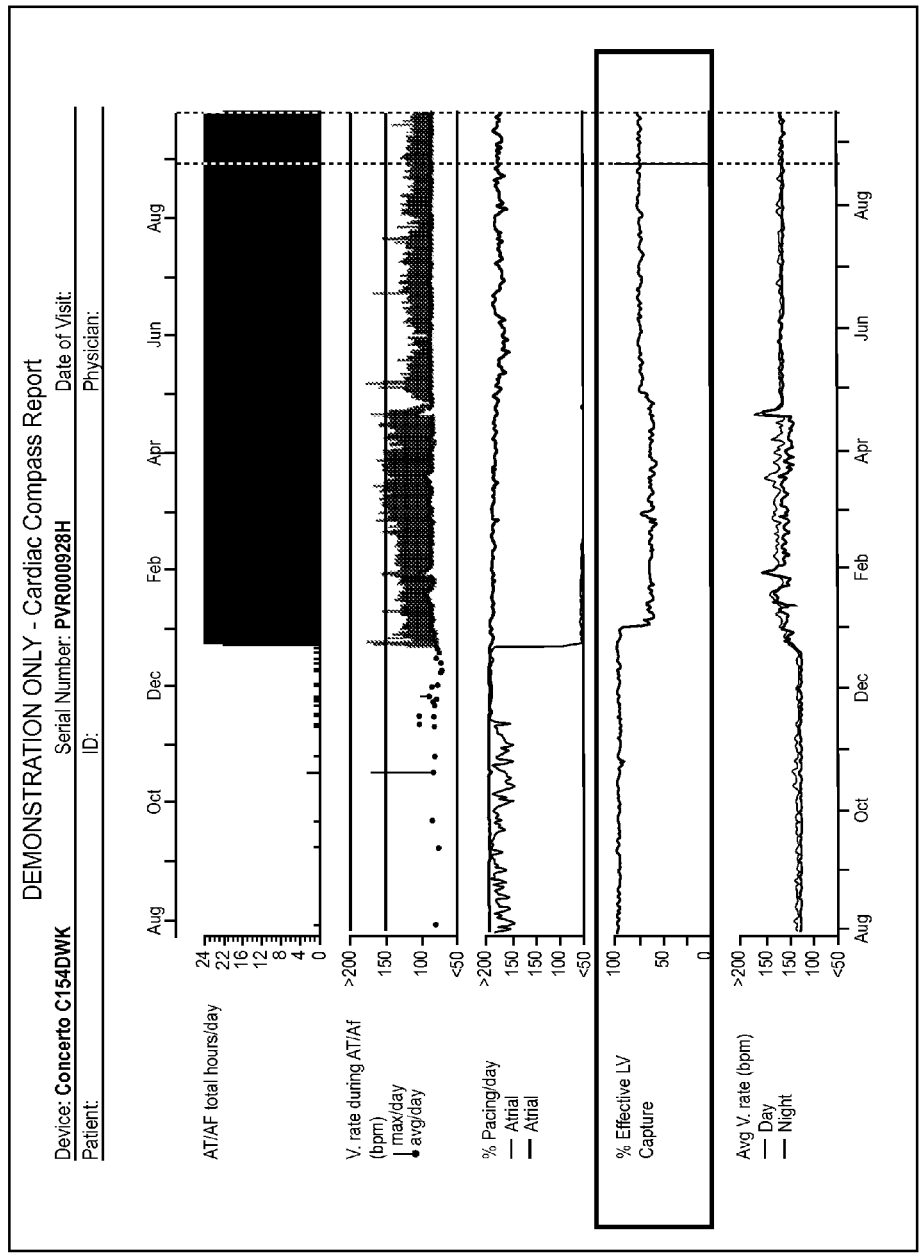
FIG. 15 is an exemplary graphical user interface that tracks heart function and device function.

As to FIG. 13, skilled artisans will appreciate that one or more of the actions can be presented to a user on a GUI before an action is implemented. Other exemplary GUIs are shown in FIGS. 14-15. FIG. 14, for example, depicts a GUI that allows for programming of device alerts for the condition of low % effective LV capture. This alert, for example, can be programmed to respond to observation of a consecutive number of days (e.g. 7 days in this case) where the measured effective LV capture is below a threshold value (e.g., 90% in this case). Alerts can be of assistance to prompting a patient to visit his or her doctor, or prompting the doctor directly to consider taking some corrective action. FIG. 15 depicts a GUI such as a Medtronic Cardiac Compass Report that reports trends over long durations of time, thus allowing a doctor to monitor heart function activity and the function of IMD 16. The addition of a daily trend of % effective LV capture to this display may help the doctor to determine the cause of loss of % effective LV capture as it relates to other physiological changes in the patient.

Figure 10:
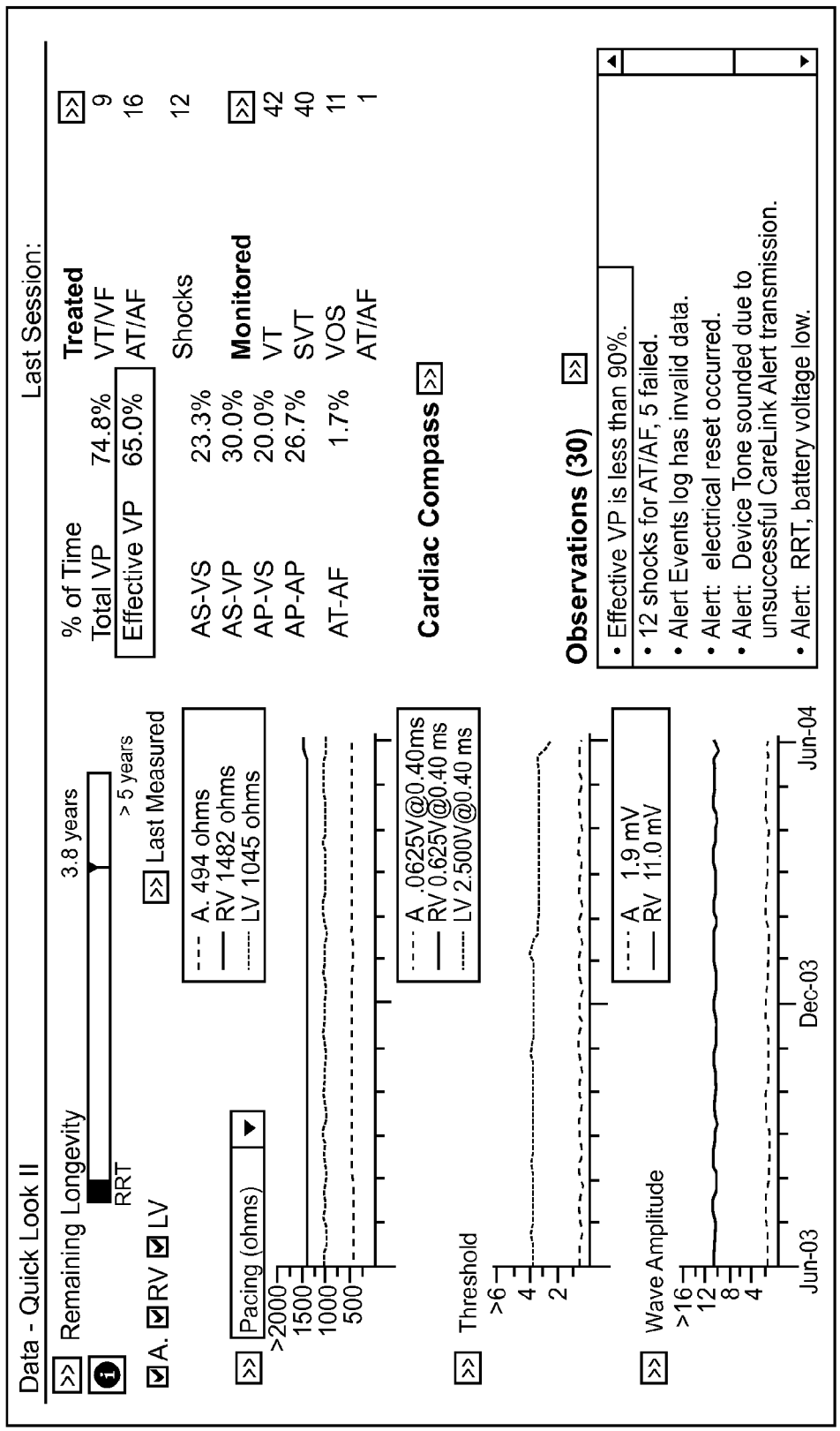
FIG. 10 is a graphical display of data obtained during evaluation of capture ineffectiveness for a pacing stimulus.

Additionally, the automated actions of FIG. 10 are not implemented during fast rhythms (e.g. average or median ventricular rate is greater than 100 bpm or average atrial rate is greater than 100 bpm) and other conditions of rate or rhythm in which LVCM is aborted.

Figure 16:
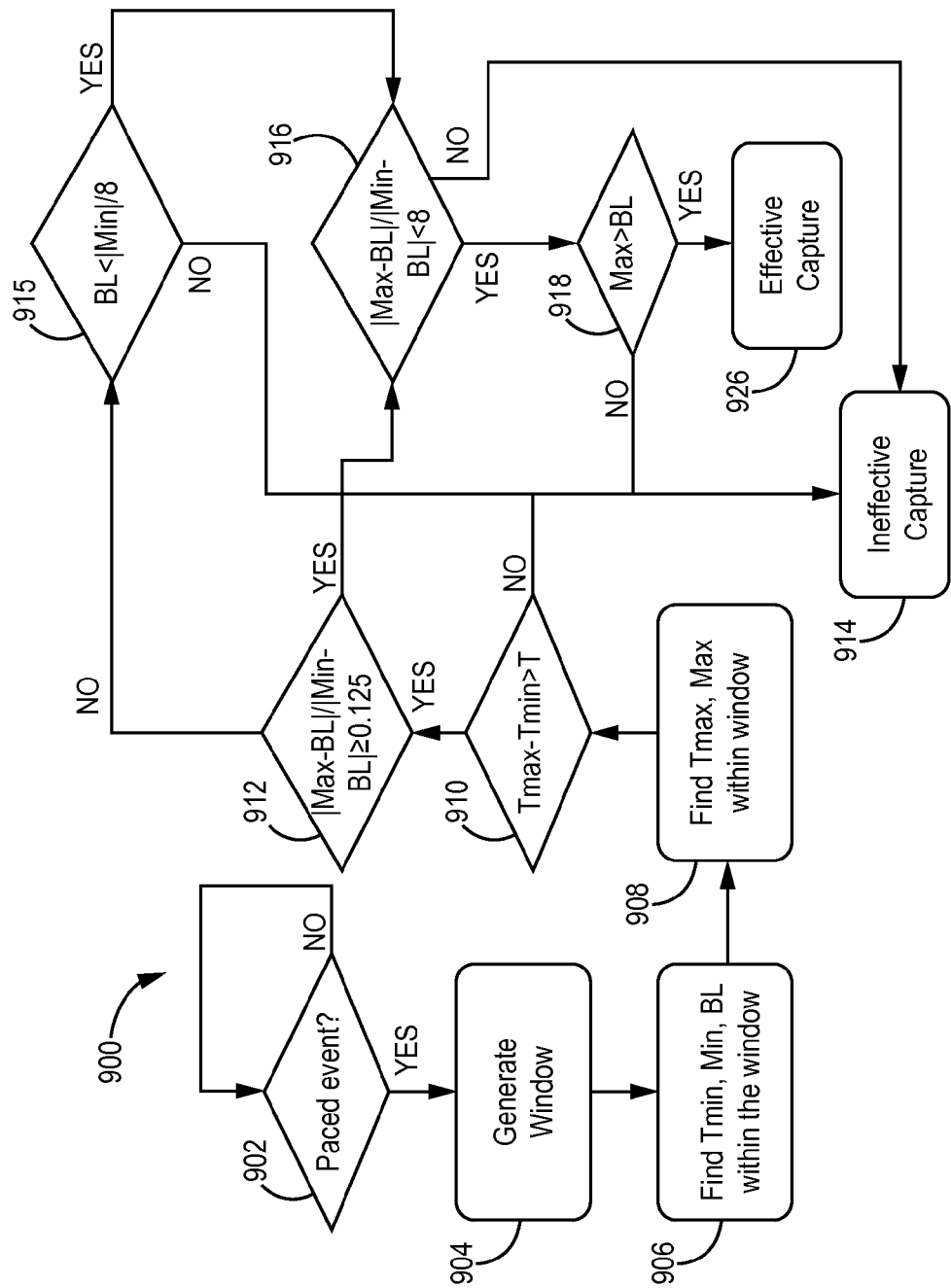
FIG. 16 is a flowchart of yet another exemplary diagnostic method for use in explaining electrical stimulus that is ineffectively capturing a ventricle.
Figure 17:
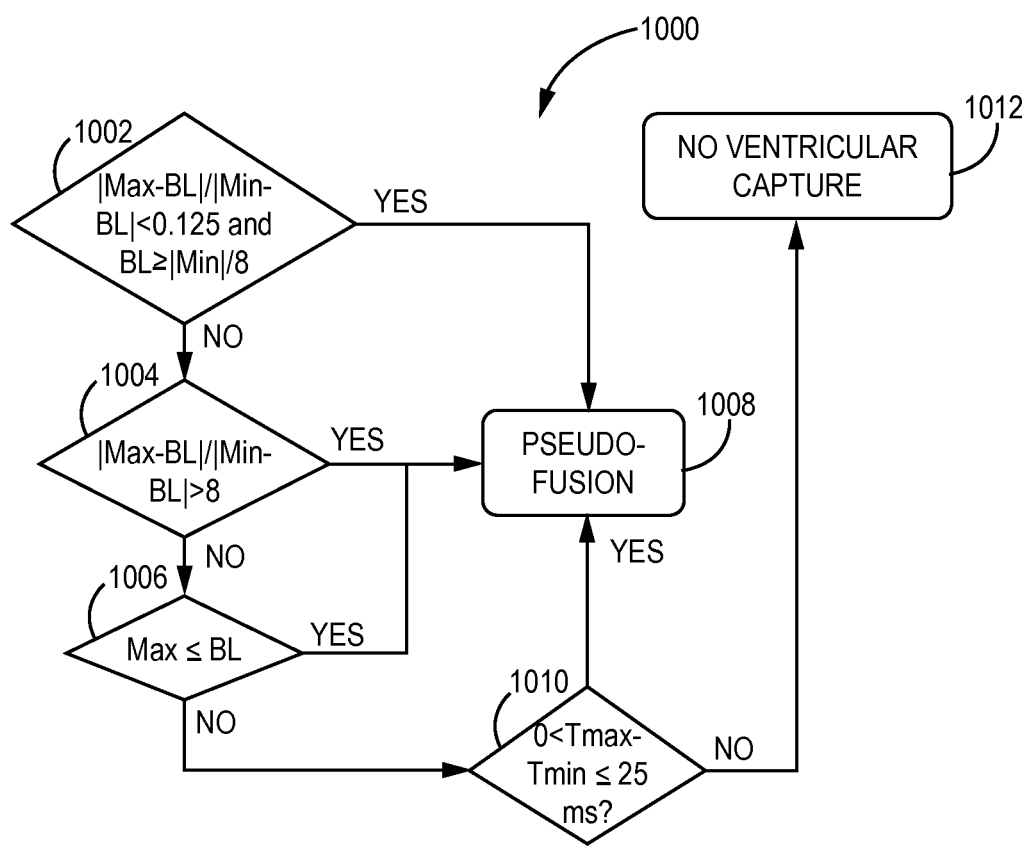
FIG. 17 is a flowchart of yet another exemplary diagnostic method for use in explaining electrical stimulus that is ineffectively capturing a ventricle.

Acronyms previously defined, for example, in the description to FIGS. 4-7, are applied in the same or similar manner as to the embodiments presented in FIG. 16 and FIG. 17. Additionally, the computer-implemented methods set forth in FIGS. 16 and/or 17 are implemented by the same or similar devices previously described herein.

FIG. 16 is a flowchart of yet another exemplary effective capture test method 900 that determines whether electrical stimulus is ineffective or effective to capture a ventricle. The effective capture test is comprised of one or more effective capture conditions set forth in blocks 910, 912, 915, 916 and 918. After applying the effective capture test, any one of the diagnostic methods disclosed herein can be applied to determine a reason for ineffective capture.

At block 902, a determination is made as to whether a current or latest ventricular event is a paced event. If the device did not deliver a paced event, the NO path is followed, returning to block 902 to continue checking for the next paced event. If a paced event has occurred, the YES path continues to block 904. At block 904, a window is created that is applied to an electrogram signal sensed via a sensing vector adjacent to or in cardiac tissue. An exemplary sensing vector may be a LV tip electrode-RV coil that is used to obtain a far field LV EGM. Another exemplary sensing vector could be the LV cathode to RV coil. In yet another embodiment, the sensing vector could be the LV cathode to Can (or housing). The window applied to the sensed EGM starts from the paced event and ends at a pre-specified amount of time (e.g. about 170 ms) after the paced event.

At block 906, the processor determines Tmin, MIN, and BL within the window created in block 904. The Tmin, MIN, and BL values are stored into memory. BL is the amplitude of the EGM signal at the start of the window, MIN is the minimum amplitude of the signal within the window, Tmin is the timing of the minimum amplitude of the signal within the window as measured from the start of the window. Storing data is performed automatically by either firmware and/or instructions herein that require results from operations to be automatically stored. At block 908, Tmax and Max are determined within the window generated at block 904. Tmax and Max are the maximum amplitude and timing of the maximum amplitude in which the maximum amplitude is determined starting from 50 ms after the paced event and ending at 170 ms after the paced event for the cardiac electrogram signal (e.g. LV far-field EGM) using techniques previously described herein. Tmax is the time-interval from pacing event to the timing of the maximum amplitude as determined above.

At block 910, a determination is made as to whether a first condition relative to effective capture is met. The first condition, presented below, subtracts Tmin from Tmax and then determines whether the result is greater than a predetermined threshold (T) such as 25 ms. The equation for the first condition can be rewritten as follows:

$$Tmax-Tmin>25 \text{ ms}$$

If Tmax−Tmin is not greater than 25 ms, then the NO path continues from block 910 to block 914 in which the pacing stimulus is declared to ineffectively capture a ventricle. In contrast, if Tmax−Tmin>25 ms, the YES path continues from block 910 to block 912.

At block 912, a determination is made as to whether |Max−BL|/|Min−BL|≥0.125. If |Max−BL|/|Min−BL| is not greater than or equal to 0.125, then the NO path continues to block 915. At block 915, a determination is made as to whether BL<|Min|/8; and, if the data establishes this statement is not true (i.e. BL is not less than |Min/8|), then the paced event is declared to ineffectively capture the ventricle such as the LV at block 914. In contrast, if the data establishes this statement (i.e. BL is less than |Min/8|), then the YES path from block 915 continues to block 916. Returning to block 912, if |Max−BL|/|Min−BL| is greater than or equal to 0.1250, then the YES path also continues to block 916.

At block 916, a determination is made as to whether |Max−BL|/|Min−BL|<8. If |Max−BL|/|Min−BL| is not less than 8, then the NO path continues from block 916 to block 914. If the condition of |Max−BL|/|Min−BL|<8 is met, then the YES path from block 916 continues to block 918.

At block 918, a determination is made as to whether Max>BL. If Max is greater than BL, then the YES path continues to block 926 in which effective capture is declared to have occurred as a result of the paced event. The result of effective capture is displayed on a graphical user interface to a user. If Max is not greater than BL, then the NO path continues to block 914 in which ineffective capture is declared to have occurred as a result of the paced event. The result of ineffective capture is displayed on a graphical user interface to a user.

FIG. 17 is a flowchart of yet another exemplary diagnostic method 1000 that provides an explanation of ineffectiveness of paced event (as determined by the logic presented in FIG. 16 ineffective). Method 1000 begins at block 1002. Block 1002 tests whether ineffective capture may be occurring due to a lower boundary (e.g. 0.125) of an effective capture condition.

Two different conditions are tested at block 1002. If the sensed data indicates |Max−BL|/|Min−BL| is less than 0.125 and BL is greater than or equal to |Min|/8, then the YES path from block 1002 continues to block 1008 in which the paced event is declared to have resulted in pseudo-fusion. Pseudo-fusion, corresponding to a paced event, is defined as the electrical activation of ventricles almost entirely through intrinsic electrical activity with no or minimal contribution of pacing. Pseudo-fusion usually occurs when the timing of the pace event is coincident with the timing of the intrinsic conduction. In such cases, even if the pace is delivered, the paced event does not play a role in electrically activating the ventricles and hence is deemed "ineffective". Returning to block 1002, if |Max−BL|/|Min−BL| is not less than 0.125 or BL is not greater than or equal to |Min|/8, then the NO path continues from block 1002 to block 1004.

At block 1006, a determination is made as to whether Max is less than or equal to BL. If Max is less than or equal to BL, the YES path continues to block 1008 and the ineffectiveness of the paced event is declared to be the result of pseudo-fusion. If Max is not less than or equal to BL, then the NO path continues from block 1006 to block 1010.

At block 1010, a determination is made as to whether 0<Tmax−Tmin≤25 ms. If 0<Tmax−Tmin≤25 ms condition is met, the YES path continues to block 1008 in which the ineffectiveness of the pacing stimuli is declared to be a result of pseudo-fusion. If Tmax−Tmin is not within the range of 0 to 25 ms such that the result is greater than zero but less than or equal to 25 ms, then the NO path continues from block 1010 to block 1012. At block 1012, the paced event is declared to be ineffective due to loss of ventricular capture. The result of the paced event not causing ventricular capture is displayed on a graphical user interface to the user. Two counters may be maintained for counting how many paced beats were ineffective due to pseudo-fusion and how many paced beats were ineffective due to loss of capture. If a paced event is found to be ineffective by the logic presented in FIG. 16, the logic in FIG. 17 is applied to determine if the cause of ineffectiveness is pseudo-fusion or loss of capture and then the corresponding counter is incremented. A graphical interface may be used to show the proportion of ineffective paced beats, and then further break it down as to how much of those were due to pseudo-fusion and how much were due to loss of capture.

Skilled artisans will also appreciate that the present disclosure encompasses embodiments in which method 600 and/or method 700 are configured to allow at most two diagnostic classifications. After reaching the second diagnostic classification, processing can shut down and IMD 16 returns to monitoring.

Skilled artisans appreciate that the ECT can be expressed with respect to positive deflection and negative deflection. For example, the present disclosure encompasses an apparatus for determining whether a ventricular pacing stimulus is capturing a paced ventricle during cardiac resynchronization therapy that comprises delivering a ventricular pacing stimulus and then sensing a signal in response to the ventricular pacing stimulus. A determination is made as to whether a positive deflection of the signal precedes a negative deflection of the signal. Thereafter, a determination is made as to whether the ventricular pacing stimulus is capturing the paced ventricle in response to determining whether the positive deflection precedes the negative deflection. The ventricular pacing stimulus does not capture the ventricle when the positive deflection precedes the negative deflection. Skilled artisans appreciate that a sensing scheme with a reverse polarity as that which is disclosed herein is still contemplated to be within the scope of the invention. For example, if a reverse polarity is used in sensing a physiological response, the opposite result would occur (i.e. ventricular pacing stimulus does capture the ventricle when the positive deflection precedes the negative deflection).

The techniques described in this disclosure, including those attributed to the IMD 16, the programmer 24, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

Listed below are co-pending U.S. patent applications that describe various aspects of the apparatus and methods described herein. The co-pending applications are incorporated by reference in their entireties.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. An apparatus for determining a reason for ineffective capture of a ventricle, comprising:
    (a) delivering means for delivering a ventricular pacing stimulus;
    (b) sensing means for sensing a signal in response to the ventricular pacing stimulus;
    (c) processing means for applying an effective capture test to the sensed data, the effective capture test comprising determining whether the ventricular pacing stimulus was effective or ineffective at capturing the ventricle based on one or more features of the signal and timing of the signal features;
    (d) means for repeatedly activating (a)-(c); and
    (e) processing means for determining the reason for ineffective capture following the repeated activation of (a)-(c), wherein determining the reason for ineffective capture comprises determining whether at least two features of the signal and timing of the at least two signal features meet one or more conditions of a set of conditions, the reason being one of pseudo-fusion or lack of ventricular capture.

2. An apparatus of claim 1 further comprising:
    processing means for determining from the signal a maximum amplitude, a maximum time associated with the occurrence of the maximum amplitude (Max), a minimum amplitude (Min), and a minimum time (Tmin) associated with the occurrence of the minimum amplitude for use in determining the reason for ineffective capture.

3. An apparatus of claim 2 wherein the set of conditions comprising:

$$|Max-baseline\ (BL)|/|Min-BL|<0.125\ and\ BL \geq |Min|/8; \quad (1)$$

$$|Max-BL|/|Min-BL|>8; \quad (2)$$

$$Max \leq BL;\ and \quad (3)$$

$$0 < Tmax - Tmin \leq 25\ ms. \quad (4)$$

4. An apparatus of claim 3 wherein responsive to determining sensed data satisfies any condition from the set of conditions, determining paced event causes pseudo-fusion.

5. An apparatus of claim 3 wherein responsive to determining sensed data does not satisfy any condition from the set of conditions, determining paced event does not cause ventricular capture.

6. A method for determining a reason for ineffective capture of a ventricle, the method comprising:
 (a) delivering a ventricular pacing stimulus;
 (b) sensing a signal in response to the ventricular pacing stimulus;
 (c) applying an effective capture test to the sensed data, the effective capture test comprising determining whether the ventricular pacing stimulus was effective or ineffective at capturing the ventricle based on one or more features of the signal and timing of the signal features;
 (d) repeatedly activating (a)-(c); and
 (e) determining the reason for ineffective capture following the repeated activation of (a)-(c), wherein determining the reason for ineffective capture comprises determining whether at least two features of the signal and timing of the at least two signal features meet one or more conditions of a set of conditions, the reason being one of pseudo-fusion or lack of ventricular capture.

7. A method of claim 6 further comprising:
 determining from the signal a maximum amplitude, a maximum time associated with the occurrence of the maximum amplitude (Max), a minimum amplitude (Min), and a minimum time (Tmin) associated with the occurrence of the minimum amplitude for use in determining the reason for ineffective capture.

8. A method of claim 7 wherein the set of conditions comprising:

$$|Max-baseline\ (BL)|/|Min-BL|<0.125\ and\ BL \geq |Min|/8; \quad (1)$$

$$|Max-BL|/|Min-BL|>8; \quad (2)$$

$$Max \leq BL;\ and \quad (3)$$

$$0 < Tmax - Tmin \leq 25\ ms. \quad (4)$$

9. A method of claim 8 wherein responsive to determining sensed data satisfies any condition from the set of conditions, determining paced event causes pseudo-fusion.

10. A method of claim 8 wherein responsive to determining sensed data does not satisfy any condition from the set of conditions, determining paced event does not cause ventricular capture.

11. A nontransitory machine readable medium containing executable computer program instructions which when executed by a data processing system cause the system to perform a method for determining a reason for ineffective capture of a ventricle, the method comprising:
 (a) delivering a ventricular pacing stimulus;
 (b) sensing a signal in response to the ventricular pacing stimulus;
 (c) applying an effective capture test to the sensed data, the effective capture test comprising determining whether the ventricular pacing stimulus was effective or ineffective at capturing the ventricle based on one or more features of the signal and timing of the signal features;
 (d) repeatedly activating (a)-(c); and
 (e) determining the reason for ineffective capture following the repeated activation of (a)-(c), wherein determining the reason for ineffective capture comprises determining whether at least two features of the signal and timing of the at least two signal features meet one or more conditions of a set of conditions, the reason being one of pseudo-fusion or lack of ventricular capture.

12. A medium as in claim 11 further comprising:
 determining from the signal a maximum amplitude, a maximum time associated with the occurrence of the maximum amplitude (Max), a minimum amplitude (Min), and a minimum time (Tmin) associated with the occurrence of the minimum amplitude for use in determining the reason for ineffective capture.

13. A medium of claim 12 wherein the set of conditions comprising:

$$|Max-baseline\ (BL)|/|Min-BL|<0.125\ and\ BL \geq |Min|/8; \quad (1)$$

$$|Max-BL|/|Min-BL|>8;\ and \quad (2)$$

$$Max \leq BL;\ and \quad (3)$$

$$0 < Tmax - Tmin \leq 25\ ms. \quad (4)$$

14. A medium of claim 13 wherein responsive to determining sensed data satisfies any condition from the set of conditions, determining paced event causes pseudo-fusion.

15. A medium of claim 13 wherein responsive to determining sensed data does not satisfy any condition from the set of conditions, determining paced event does not cause ventricular capture.

16. A nontransitory machine readable medium containing executable computer program instructions which when executed by a data processing system cause the system to perform a method for determining a reason for ineffective capture of a ventricle, the method comprising:
 (a) delivering a ventricular pacing stimulus;
 (b) sensing a signal in response to the ventricular pacing stimulus;
 (c) applying an effective capture test to the sensed data, the effective capture test comprising determining whether the ventricular pacing stimulus was effective or ineffective at capturing the ventricle based on one or more features of the signal and timing of the signal features;
 (d) repeatedly activating (a)-(c);
 (e) determining the reason for ineffective capture following the repeated activation of (a)-(c), the reason being one of pseudo-fusion or lack of ventricular capture; and
 (f) processing a set of conditions to determine the reason for ineffective capture, wherein the set of conditions comprising:

$$|Max-baseline\ (BL)|/|Min-BL|<0.125\ and\ BL \geq |Min|/8; \quad (1)$$

$$|Max-BL|/|Min-BL|>8; \quad (2)$$

$$Max \leq BL;\ and \quad (3)$$

$$0 < Tmax - Tmin \leq 25\ ms. \quad (4)$$

17. A medium of claim 16 wherein responsive to determining sensed data satisfies any condition from the set of conditions, determining paced event causes pseudo-fusion.

18. A medium of claim 16 wherein responsive to determining sensed data does not satisfy any condition from the set of conditions, determining paced event does not cause ventricular capture.

19. An apparatus for determining a reason for ineffective capture of a ventricle, comprising:
 (a) delivering means for delivering means for delivering a ventricular pacing stimulus;

(b) sensing means for sensing a signal in response to the ventricular pacing stimulus;
(c) processing means for applying an effective capture test to the sensed data, the effective capture test comprising determining whether the ventricular pacing stimulus was effective or ineffective at capturing the ventricle based on one or more features of the signal and timing of the signal features;
(d) means for repeatedly activating (a)-(c);
(e) processing means for determining the reason for ineffective capture following the repeated activation of (a)-(c), the reason being one of pseudo-fusion or lack of ventricular capture; and
(f) processing means for processing a set of conditions to determine the reason for ineffective capture,
wherein the processing means comprises processing means for determining from the signal a maximum amplitude, a maximum time associated with the maximum amplitude (Max), a minimum amplitude (Min), and a minimum time (Tmin) associated with the minimum amplitude, and
further wherein the set of conditions comprising:

$$|\text{Max}-\text{baseline (BL)}|/|\text{Min}-\text{BL}|<0.125 \text{ and } \text{BL} \geq |\text{Min}|/8; \quad (1)$$

$$|\text{Max}-\text{BL}|/|\text{Min}-\text{BL}|>8; \quad (2)$$

$$\text{Max} \leq \text{BL}; \text{ and} \quad (3)$$

$$0 < T\text{max} - T\text{min} \leq 25 \text{ ms.} \quad (4)$$

20. An apparatus of claim 19 wherein responsive to determining sensed data satisfies any condition from the set of conditions, determining paced event causes pseudo-fusion.

* * * * *